US011976114B2

(12) United States Patent
Chedid et al.

(10) Patent No.: US 11,976,114 B2
(45) Date of Patent: May 7, 2024

(54) COMPOUNDS AND METHODS TARGETING INTERLEUKIN-34

(71) Applicant: Eli Lilly and Company, Indianapolis, IN (US)

(72) Inventors: Marcio Chedid, Fishers, IN (US); Adam S. Fleisher, Indianapolis, IN (US); Megan Brittany Lannan, Fishers, IN (US); Albert Lo, Indianapolis, IN (US); Mark Mintun, Indianapolis, IN (US); Victor H. Obungu, McCordsville, IN (US); Sarah Elisabeth Raines, Avon, IN (US); John Randall Sims, II, Zionsville, IN (US); Andrew Dixon Skora, Solana Beach, CA (US); Robin Elizabeth Walsh, Carmel, IN (US); Elizabeth Anne West, San Diego, CA (US); Ming Ye, Carmel, IN (US)

(73) Assignee: ELI Lilly and Company, Indianapolis, IN (US)

( * ) Notice: Subject to any disclaimer, the term of this patent is extended or adjusted under 35 U.S.C. 154(b) by 0 days.

(21) Appl. No.: 18/050,227

(22) Filed: Oct. 27, 2022

(65) Prior Publication Data
US 2023/0279094 A1 Sep. 7, 2023

Related U.S. Application Data

(60) Provisional application No. 63/273,216, filed on Oct. 29, 2021.

(51) Int. Cl.
*C07K 16/24* (2006.01)
*A61K 39/00* (2006.01)
*C07K 16/18* (2006.01)

(52) U.S. Cl.
CPC ............ *C07K 16/244* (2013.01); *C07K 16/18* (2013.01); *A61K 39/00* (2013.01)

(58) Field of Classification Search
CPC .. C07K 16/244; C07K 16/18; C07K 2317/77; C07K 2317/21; C07K 2317/33; C07K 2317/76; C07K 2317/92; C07K 2317/94; A61K 39/00; A61K 2039/505; A61K 2039/507; A61K 2039/54; A61K 2039/545; A61P 25/28
See application file for complete search history.

(56) References Cited

U.S. PATENT DOCUMENTS 10,703,813 B2 7/2020 Heymann et al.
2016/0297885 A1* 10/2016 Kuo et al.

FOREIGN PATENT DOCUMENTS

| WO | WO-2012019061 A2 * | 2/2012 | ......... A61K 39/0011 |
|---|---|---|---|
| WO | 2013/119716 A1 | 8/2013 | |
| WO | 2016/016262 A1 | 2/2016 | |
| WO | 2016/097420 A1 | 6/2016 | |
| WO | 2016/196679 A1 | 12/2016 | |
| WO | 2018/005282 A1 | 1/2018 | |
| WO | 2018/031361 A2 | 2/2018 | |
| WO | 2018/194951 A1 | 10/2018 | |
| WO | 2019/169291 A1 | 9/2019 | |

OTHER PUBLICATIONS

The International Searching Authority, International Search Report, for PCT/US2022/078776, filed Oct. 22, 2022, WO, dated Feb. 2, 2023.
The Written Opinion of the International Searching Authority, for PCT/US2022/078776, filed on Oct. 27, 2022, WO.
Mintun, et al., "Donanemab in Early Alzheimer's Disease", The New England Journal of Medicine, vol. 384, No. 18, May 6, 2021, pp. 1691-1704.
Becher, et al, Cytokine networks in neuroinflammation, Institute of Experimental Immunology, University of Zurich, Zurich 8057, Switzerland, Department of Immunology, University of Washington, Seattle, Washington, USA, pp. 1-11, 2016.
Felix, et al, Structure and Assembly Mechanism of the Signaling Complex Mediated by Human CSF-1, CellPress, Structure Article, pp. 1621-1636.
Wang, et al, Interkeukin-34, a cytokine crucial for the differentiation and maintenance of tissue resident macrophages and Langerhans cells, Department of Pathology and Immunology, Washington University School of Medicine, St. Louis, MO, USA, Eur J Immunol. Jun. 2014; 44(6) 1575-1581.

* cited by examiner

*Primary Examiner* — Jeffrey Stucker
*Assistant Examiner* — Duncan Groebe
(74) *Attorney, Agent, or Firm* — Dan L. Wood

(57) ABSTRACT

The present disclosure relates to IL-34 antibodies, compositions comprising the same, and methods of using the antibodies and or compositions thereof for treating immune-mediated diseases such as neurodegenerative diseases, for example Alzheimer's Disease or a tauopathy disease.

5 Claims, 2 Drawing Sheets
Specification includes a Sequence Listing.

SEQUENCE LISTING

```
Sequence total quantity: 41
SEQ ID NO: 1              moltype = AA  length = 445
FEATURE                   Location/Qualifiers
source                    1..445
                          mol_type = protein
                          organism = synthetic construct
SEQUENCE: 1
EVQLLESGGG LVQPGGSLRL SCAASGFAFS NYAMSWVRQA PGKGLEWVSA ISASGGKTYY  60
ADSVKGRFTI SRDNSKNTLY LQMNSLRAED TAVYYCAKRG YLWHAFDHWG RGTLVTVSSA 120
STKGPSVFPL APCSRSTSES TAALGCLVKD YFPEPVTVSW NSGALTSGVH TFPAVLQSSG 180
LYSLSSVVTV PSSSLGTKTY TCNVDHKPSN TKVDKRVESK YGPPCPPCPA PEAAGGPSVF 240
LFPPKPKDTL MISRTPEVTC VVVDVSQEDP EVQFNWYVDG VEVHNAKTKP REEQFNSTYR 300
VVSVLTVLHQ DWLNGKEYKC KVSNKGLPSS IEKTISKAKG QPREPQVYTL PPSQEEMTKN 360
QVSLTCLVKG FYPSDIAVEW ESNGQPENNY KTTPPVLDSD GSFFLYSRLT VDKSRWQEGN 420
VFSCSVMHEA LHNHYTQKSL SLSLG                                     445

SEQ ID NO: 2              moltype = AA  length = 216
FEATURE                   Location/Qualifiers
source                    1..216
                          mol_type = protein
                          organism = synthetic construct
SEQUENCE: 2
EIVLTQSPGT LSLSPGERAT LSCRASQSVS SLYLAWYQQK PGQAPRLLIY GASSRATGIP  60
DRFSGSGSGT DFTLTISRLE PEDFAVYYCQ VVGSSPPFTF GGGTKVEIKR TVAAPSVFIF 120
PPSDEQLKSG TASVVCLLNN FYPREAKVQW KVDNALQSGN SQESVTEQDS KDSTYSLSST 180
```

LTLSKADYEK HKVYACEVTH QGLSSPVTKS FNRGEC                                          216

SEQ ID NO: 3            moltype = AA   length = 108
FEATURE                 Location/Qualifiers
source                  1..108
                        mol_type = protein
                        organism = synthetic construct
SEQUENCE: 3
EVQLLESGGG LVQPGGSLRL SCAASGFAFS NYAMSWVRQA PGKGLEWVSA ISASGGKTYY               60
ADSVKGRFTI SRDNSKNTLY LQMNSLRAED TAVYYCAKRG YLWHAFDH                            108

SEQ ID NO: 4            moltype = AA   length = 99
FEATURE                 Location/Qualifiers
source                  1..99
                        mol_type = protein
                        organism = synthetic construct
SEQUENCE: 4
EIVLTQSPGT LSLSPGERAT LSCRASQSVS SLYLAWYQQK PGQAPRLLIY GASSRATGIP               60
DRFSGSGSGT DFTLTISRLE PEDFAVYYCQ VVGSSPPFT                                      99

SEQ ID NO: 5            moltype = AA   length = 13
FEATURE                 Location/Qualifiers
source                  1..13
                        mol_type = protein
                        organism = synthetic construct
SEQUENCE: 5
AASGFAFSNY AMS                                                                   13

SEQ ID NO: 6            moltype = AA   length = 10
FEATURE                 Location/Qualifiers
source                  1..10
                        mol_type = protein
                        organism = synthetic construct
SEQUENCE: 6
AISASGGKTY                                                                       10

SEQ ID NO: 7            moltype = AA   length = 12
FEATURE                 Location/Qualifiers
source                  1..12
                        mol_type = protein
                        organism = synthetic construct
SEQUENCE: 7
AKRGYLWHAF DH                                                                    12

SEQ ID NO: 8            moltype = AA   length = 12
FEATURE                 Location/Qualifiers
source                  1..12
                        mol_type = protein
                        organism = synthetic construct
SEQUENCE: 8
RASQSVSSLY LA                                                                    12

SEQ ID NO: 9            moltype = AA   length = 8
FEATURE                 Location/Qualifiers
source                  1..8
                        mol_type = protein
                        organism = synthetic construct
SEQUENCE: 9
YGASSRAT                                                                         8

SEQ ID NO: 10           moltype = AA   length = 10
FEATURE                 Location/Qualifiers
source                  1..10
                        mol_type = protein
                        organism = synthetic construct
SEQUENCE: 10
QVVGSSPPFT                                                                       10

SEQ ID NO: 11           moltype = DNA  length = 1335
FEATURE                 Location/Qualifiers
source                  1..1335
                        mol_type = other DNA
                        organism = synthetic construct
SEQUENCE: 11
gaagtccagt tgctggaatc tggcggcggt ctcgttcagc caggggggcag cttgcgtctt              60
agttgtgcag catccggggtt tgccttttcc aattacgcta tgtcatgggt aaggcaagcc              120
ccaggcaaag gactcgaatg ggtttccgcc attagtgcct caggaggcaa gacatactat              180
gccgattctg taaagggcag atttactata tctcgggaca attctaaaaa tacactctat              240
cttcagatga atagccttag agctgaagat accgctgtct actactgtgc caaacgtggc              300

```
tacctttggc acgcctttga tcactggggt cggggtactc tcgtaactgt aagctccgcc  360
tccaccaagg gcccatcggt cttcccgcta gcgccctgct ccaggagcac ctccgagagc  420
acagccgccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac gaagacctac  600
acctgcaacg tagatcacaa gcccagcaac accaaggtgg acaagagagt tgagtccaaa  660
tatggtcccc catgcccacc ctgcccagca cctgaggccg ccggggggacc atcagtcttc  720
ctgttccccc caaaacccaa ggacactctc atgatctccc ggacccctga ggtcacgtgc  780
gtggtggtgg acgtgagcca ggaagacccc gaggtccagt tcaactggta cgtggatggc  840
gtggaggtgc ataatgccaa gacaaagccg cgggaggagc agttcaacag cacgtaccgt  900
gtggtcagcg tcctcaccgt cctgcaccag gactggctga acggcaagga gtacaagtgc  960
aaggtctcca acaaaggcct cccgtcctcc atcgagaaaa ccatctccaa agccaaaggg 1020
cagccccgag agccacaggt gtacaccctg cccccatccc aggaggagat gaccaagaac 1080
caggtcagcc tgacctgcct ggtcaaaggc ttctaccccca gcgacatcgc cgtggagtgg 1140
gaaagcaatg ggcagccgga gaacaactac aagaccacgc ctcccgtgct ggactccgac 1200
ggctccttct tcctctacag caggctaacc gtggacaaga gcaggtggca ggaggggaat 1260
gtcttctcat gctccgtgat gcatgaggct ctgcacaacc actacacaca gaagagcctc 1320
tccctgtctc tgggt                                                  1335

SEQ ID NO: 12           moltype = DNA  length = 648
FEATURE                 Location/Qualifiers
source                  1..648
                        mol_type = other DNA
                        organism = synthetic construct
SEQUENCE: 12
gaaatagttc tcactcagtc ccctgggaca ctctccctga gtccaggaga acgtgcaaca   60
ctcagttgcc gtgcaagcca gtccgtctca tccttgtatc ttgcttggta ccaacaaaaa  120
cctggacagg cccccccgtct tcttatctat ggtgcctcca gtcgcgcaac tggtattccc  180
gaccggttca gcggcagtgg gtccggcact gacttcaccc tgactataag tcggttggag  240
ccagaggact ttgccgtgta ctattgccaa gtggtggaga gctcccctcc cttcactttc  300
ggcggaggga ccaaggtaga aatcaaaaga actgtggcgg cgccatctgt cttcatcttc  360
ccgccatctg atgagcagtt gaaatccgga actgcctctg ttgtgtgcct gctgaataac  420
ttctatccca gagaggccaa agtacagtgg aaggtggata acgccctcca atcgggtaac  480
tcccaggaga gtgtcacaga gcaggacagc aaggacagcc cctacagcct cagcagcacc  540
ctgacgctga gcaaagcaga ctacgagaaa cacaaagtct acgcctgcga agtcacccat  600
cagggcctga gctcgcccgt cacaaagagc ttcaacaggg gagagtgc              648

SEQ ID NO: 13           moltype = AA  length = 5
FEATURE                 Location/Qualifiers
source                  1..5
                        mol_type = protein
                        organism = synthetic construct
SEQUENCE: 13
NYAMS                                                                5

SEQ ID NO: 14           moltype = AA  length = 17
FEATURE                 Location/Qualifiers
source                  1..17
                        mol_type = protein
                        organism = synthetic construct
SEQUENCE: 14
AISASGGKTY YADSVKG                                                  17

SEQ ID NO: 15           moltype = AA  length = 10
FEATURE                 Location/Qualifiers
source                  1..10
                        mol_type = protein
                        organism = synthetic construct
SEQUENCE: 15
RGYLWHAFDH                                                          10

SEQ ID NO: 16           moltype = AA  length = 12
FEATURE                 Location/Qualifiers
source                  1..12
                        mol_type = protein
                        organism = synthetic construct
SEQUENCE: 16
RASQSVSSLY LA                                                       12

SEQ ID NO: 17           moltype = AA  length = 7
FEATURE                 Location/Qualifiers
source                  1..7
                        mol_type = protein
                        organism = synthetic construct
SEQUENCE: 17
GASSRAT                                                              7

SEQ ID NO: 18           moltype = AA  length = 10
FEATURE                 Location/Qualifiers
```

```
source                      1..10
                            mol_type = protein
                            organism = synthetic construct
SEQUENCE: 18
QVVGSSPPFT                                                                  10

SEQ ID NO: 19               moltype = AA  length = 7
FEATURE                     Location/Qualifiers
source                      1..7
                            mol_type = protein
                            organism = synthetic construct
SEQUENCE: 19
GFAFSNY                                                                      7

SEQ ID NO: 20               moltype = AA  length = 6
FEATURE                     Location/Qualifiers
source                      1..6
                            mol_type = protein
                            organism = synthetic construct
SEQUENCE: 20
SASGGK                                                                       6

SEQ ID NO: 21               moltype = AA  length = 10
FEATURE                     Location/Qualifiers
source                      1..10
                            mol_type = protein
                            organism = synthetic construct
SEQUENCE: 21
RGYLWHAFDH                                                                  10

SEQ ID NO: 22               moltype = AA  length = 12
FEATURE                     Location/Qualifiers
source                      1..12
                            mol_type = protein
                            organism = synthetic construct
SEQUENCE: 22
RASQSVSSLY LA                                                               12

SEQ ID NO: 23               moltype = AA  length = 7
FEATURE                     Location/Qualifiers
source                      1..7
                            mol_type = protein
                            organism = synthetic construct
SEQUENCE: 23
GASSRAT                                                                      7

SEQ ID NO: 24               moltype = AA  length = 10
FEATURE                     Location/Qualifiers
source                      1..10
                            mol_type = protein
                            organism = synthetic construct
SEQUENCE: 24
QVVGSSPPFT                                                                  10

SEQ ID NO: 25               moltype = AA  length = 8
FEATURE                     Location/Qualifiers
source                      1..8
                            mol_type = protein
                            organism = synthetic construct
SEQUENCE: 25
GFAFSNYA                                                                     8

SEQ ID NO: 26               moltype = AA  length = 8
FEATURE                     Location/Qualifiers
source                      1..8
                            mol_type = protein
                            organism = synthetic construct
SEQUENCE: 26
ISASGGKT                                                                     8

SEQ ID NO: 27               moltype = AA  length = 12
FEATURE                     Location/Qualifiers
source                      1..12
                            mol_type = protein
                            organism = synthetic construct
SEQUENCE: 27
AKRGYLWHAF DH                                                               12

SEQ ID NO: 28               moltype = AA  length = 7
```

```
FEATURE                 Location/Qualifiers
source                  1..7
                        mol_type = protein
                        organism = synthetic construct
SEQUENCE: 28
QSVSSLY                                                                    7

SEQ ID NO: 29           moltype =    length =
SEQUENCE: 29
000

SEQ ID NO: 30           moltype = AA   length = 10
FEATURE                 Location/Qualifiers
source                  1..10
                        mol_type = protein
                        organism = synthetic construct
SEQUENCE: 30
QVVGSSPPFT                                                                10

SEQ ID NO: 31           moltype = AA   length = 222
FEATURE                 Location/Qualifiers
source                  1..222
                        mol_type = protein
                        organism = Homo sapiens
SEQUENCE: 31
NEPLEMWPLT QNEECTVTGF LRDKLQYRSR LQYMKHYFPI NYKISVPYEG VFRIANVTRL           60
QRAQVSEREL RYLWVLVSLS ATESVQDVLL EGHPSWKYLQ EVETLLLNVQ QGLTDVEVSP          120
KVESVLSLLN APGPNLKLVR PKALLDNCFR VMELLYCSCC KQSSVLNWQD CEVPSPQSCS          180
PEPSLQYAAT QLYPPPPWSP SSPPHSTGSV RPVRAQGEGL LP                             222

SEQ ID NO: 32           moltype = AA   length = 12
FEATURE                 Location/Qualifiers
source                  1..12
                        mol_type = protein
                        organism = synthetic construct
SEQUENCE: 32
ESKYGPPCPP CP                                                              12

SEQ ID NO: 33           moltype = AA   length = 216
FEATURE                 Location/Qualifiers
source                  1..216
                        mol_type = protein
                        organism = synthetic construct
SEQUENCE: 33
APEAAGGPSV FLFPPKPKDT LMISRTPEVT CVVVDVSQED PEVQFNWYVD GVEVHNAKTK           60
PREEQFNSTY RVVSVLTVLH QDWLNGKEYK CKVSNKGLPS SIEKTISKAK GQPREPQVYT          120
LPPSQEEMTK NQVSLTCLVK GFYPSDIAVE WESNGQPENN YKTTPPVLDS DGSFFLYSRL          180
TVDKSRWQEG NVFSCSVMHE ALHNHYTQKS LSLSLG                                   216

SEQ ID NO: 34           moltype = AA   length = 726
FEATURE                 Location/Qualifiers
source                  1..726
                        mol_type = protein
                        organism = Macaca fascicularis
SEQUENCE: 34
IPVIEPSGPE LVVKPGETVT LRCVGNGSVE WDGPISPHWT LYSDGPSSVL TTNNATFQNT           60
RTYRCTEPGD PLGGSAAIHL YVKDPARPWN VLAKEVVVPE DQDALLPCLL TDPVLEAGVS          120
LVRLRGRPLL RHTNYSFSPW HGFIIHRAKF IQGQDYQCSA LMGGRKVMSI SIRLKVQKVI          180
PGPPALTLVP AELVRIRGEA AQIVCSASNI DVDFDVFLQN NTTKLAIPQR SDFHDNRYQK          240
VLTLSLSLGQVD FQHAGNYSCV ASNVQGKHST SMFFRVVESA YLDLSSEQNL IQEVTVGEGL        300
NLKVMVEAYP GLQGFNWTYL GPFSDHQPEP KLANATTKDT YRHTFTLSLP RLKPSEAGRY          360
SFLARNPGGW RALTFELTLR YPPEVSVIWT SINGSGTLLC AASGYPQPNV TWLQCAGHTD          420
RCDEAQVLQV WVDPHPEVLS QEPFQKVTVQ SLLTAETLEH NQTYECRAHN SVGSGSWAFI          480
PISAGARTHP PDEAAAEPKS SDKTHTCPPC PAPELLGGPS VFLFPPKPKD TLMISRTPEV          540
TCVVVDVSHE DPEVKFNWYV DGVEVHNAKT KPREEQYNST YRVVSVLTVL HQDWLNGKEY          600
KCKVSNKALP APIEKTISKA KGQPREPQVY TLPPSRDELT KNQVSLTCLV KGFYPSDIAV          660
EWESNGQPEN NYKTTPPVLD SDGSFFLYSK LTVDKSRWQQ GNVFSCSVMH EALHNHYTQK          720
SLSLSP                                                                    726

SEQ ID NO: 35           moltype = AA   length = 449
FEATURE                 Location/Qualifiers
source                  1..449
                        mol_type = protein
                        organism = synthetic construct
SEQUENCE: 35
EVQLLESGGG LVQPGGSLRL SCAASGFAFS NYAMSWVRQA PGKGLEWVSA ISASGGKTYY           60
ADSVKGRFTI SRDNSKNTLY LQMNSLRAED TAVYYCAKRG YLWHAFDHWG RGTLVTVSSA          120
STKGPSVFPL APSSKSTSGG TAALGCLVKD YFPEPVTVSW NSGALTSGVH TFPAVLQSSG          180
LYSLSSVVTV PSSSLGTQTY ICNVNHKPSN TKVDKRVEPK SCDKTHTCPP CPAPEAEGAP          240
```

```
SVFLFPPKPK DTLMISRTPE VTCVVVDVSH EDPEVKFNWY VDGVEVHNAK TKPREEQYNS     300
TYRVVSVLTV LHQDWLNGKE YKCKVSNKAL PSSIEKTISK AKGQPREPQV YTLPPSREEM     360
TKNQVSLTCL VKGFYPSDIA VEWESNGQPE NNYKTTPPVL DSDGSFFLYS KLTVDKSRWQ     420
QGNVFSCSVM HEALHNHYTQ KSLSLSPGK                                       449

SEQ ID NO: 36          moltype = AA   length = 448
FEATURE                Location/Qualifiers
source                 1..448
                       mol_type = protein
                       organism = synthetic construct
SEQUENCE: 36
EVQLLESGGG LVQPGGSLRL SCAASGFAFS NYAMSWVRQA PGKGLEWVSA ISASGGKTYY     60
ADSVKGRFTI SRDNSKNTLY LQMNSLRAED TAVYYCAKRG YLWHAFDHWG RGTLVTVSSA     120
STKGPSVFPL APSSKSTSGG TAALGCLVKD YFPEPVTVSW NSGALTSGVH TFPAVLQSSG     180
LYSLSSVVTV PSSSLGTQTY ICNVNHKPSN TKVDKKVEPK SCDKTHTCPP CPAPELLGGP     240
SVFLFPPKPK DTLMISRTPE VTCVVVDVSH EDPEVKFNWY VDGVEVHNAK TKPREEQYNS     300
TYRVVSVLTV LHQDWLNGKE YKCKVSNKAL PAPIEKTISK AKGQPREPQV YTLPPSRDEL     360
TKNQVSLTCL VKGFYPSDIA VEWESNGQPE NNYKTTPPVL DSDGSFFLYS KLTVDKSRWQ     420
QGNVFSCSVM HEALHNHYTQ KSLSLSPG                                        448

SEQ ID NO: 37          moltype = AA   length = 444
FEATURE                Location/Qualifiers
source                 1..444
                       mol_type = protein
                       organism = synthetic construct
SEQUENCE: 37
EVQLLESGGG LVQPGGSLRL SCAASGFAFS NYAMSWVRQA PGKGLEWVSA ISASGGKTYY     60
ADSVKGRFTI SRDNSKNTLY LQMNSLRAED TAVYYCAKRG YLWHAFDHWG RGTLVTVSSA     120
STKGPSVFPL APCSRSTSES TAALGCLVKD YFPEPVTVSW NSGALTSGVH TFPAVLQSSG     180
LYSLSSVVTV PSSNFGTQTY TCNVDHKPSN TKVDKTVERK CCVECPPCPA PPVAGPSVFL     240
FPPKPKDTLM ISRTPEVTCV VVDVSHEDPE VQFNWYVDGV EVHNAKTKPR EEQFNSTFRV     300
VSVLTVVHQD WLNGKEYKCK VSNKGLPAPI EKTISKTKGQ PREPQVYTLP PSREEMTKNQ     360
VSLTCLVKGF YPSDIAVEWE SNGQPENNYK TTPPMLDSDG SFFLYSKLTV DKSRWQQGNV     420
FSCSVMHEAL HNHYTQKSLS LSPG                                            444

SEQ ID NO: 38          moltype = AA   length = 444
FEATURE                Location/Qualifiers
source                 1..444
                       mol_type = protein
                       organism = synthetic construct
SEQUENCE: 38
QVQLVQSGAE VKKPGSSVKV SCKASGYDFT RYYINWVRQA PGQGLEWMGW INPGSGNTKY     60
NEKFKGRVTI TADESTSTAY MELSSLRSED TAVYYCAREG ITVYWGQGTT VTVSSASTKG     120
PSVFPLAPSS KSTSGGTAAL GCLVKDYFPE PVTVSWNSGA LTSGVHTFPA VLQSSGLYSL     180
SSVVTVPSSS LGTQTYICNV NHKPSNTKVD KKVEPKSCDK THTCPPCPAP ELLGGPSVFL     240
FPPKPKDTLM ISRTPEVTCV VVDVSHEDPE VKFNWYVDGV EVHNAKTKPR EEQYNSTYRV     300
VSVLTVLHQD WLNGKEYKCK VSNKALPAPI EKTISKAKGQ PREPQVYTLP PSRDELTKNQ     360
VSLTCLVKGF YPSDIAVEWE SNGQPENNYK TTPPVLDSDG SFFLYSKLTV DKSRWQQGNV     420
FSCSVMHEAL HNHYTQKSLS LSPG                                            444

SEQ ID NO: 39          moltype = AA   length = 219
FEATURE                Location/Qualifiers
source                 1..219
                       mol_type = protein
                       organism = synthetic construct
SEQUENCE: 39
DIVMTQTPLS LSVTPGQPAS ISCKSSQSLL YSRGKTYLNW LLQKPGQSPQ LLIYAVSKLD     60
SGVPDRFSGS GSGTDFTLKI SRVEAEDVGV YYCVQGTHYP FTFGQGTKLE IKRTVAAPSV     120
FIFPPSDEQL KSGTASVVCL LNNFYPREAK VQWKVDNALQ SGNSQESVTE QDSKDSTYSL     180
SSTLTLSKAD YEKHKVYACE VTHQGLSSPV TKSFNRGEC                            219

SEQ ID NO: 40          moltype = AA   length = 451
FEATURE                Location/Qualifiers
source                 1..451
                       mol_type = protein
                       organism = synthetic construct
SEQUENCE: 40
EVQLLESGGG LVQPGGSLRL SCAASGFTFS SYPMSWVRQA PGKGLEWVSA ISGSGGSTYY     60
ADSVKGRFTI SRDNSKNTLY LQMNSLRAED TAVYYCAREG GSGSYYNGFD YWGQGTLVTV     120
SSASTKGPSV FPLAPSSKST SGGTAALGCL VKDYFPEPVT VSWNSGALTS GVHTFPAVLQ     180
SSGLYSLSSV VTVPSSSLGT QTYICNVNHK PSNTKVDKKV EPKSCDKTHT CPPCPAPELL     240
GGPSVFLFPP KPKDTLMISR TPEVTCVVVD VSHEDPEVKF NWYVDGVEVH NAKTKPREEQ     300
YNSTYRVVSV LTVLHQDWLN GKEYKCKVSN KALPAPIEKT ISKAKGQPRE PQVYTLPPSR     360
DELTKNQVSL TCLVKGFYPS DIAVEWESNG QPENNYKTTP PVLDSDGSFF LYSKLTVDKS     420
RWQQGNVFSC SVMHEALHNH YTQKSLSLSP G                                    451

SEQ ID NO: 41          moltype = AA   length = 214
FEATURE                Location/Qualifiers
source                 1..214
```

```
                    mol_type = protein
                    organism = synthetic construct
SEQUENCE: 41
DIQMTQSPST LSASVGDRVT ITCRASQSLG NWLAWYQQKP GKAPKLLIYQ ASTLESGVPS    60
RFSGSGSGTE FTLTISSLQP DDFATYYCQH YKGSFWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214
```

COMPOUNDS AND METHODS TARGETING INTERLEUKIN-34

SEQUENCE LISTING FILE

The present application is being filed along with a Sequence Listing in ST.26 XML format. The Sequence Listing is provided as a file titled "30105_SequenceListing" created Mar. 16, 2023 and is 42 kilobytes in size. The Sequence Listing information in the ST.26 XML format is incorporated herein by reference in its entirety.

The present disclosure relates to compounds, pharmaceutical compositions, and methods, which include antibodies directed against human interleukin-34 (IL-34), which are expected to be useful in the field of neuroinflammation and acute or chronic inflammatory diseases. In particular, the embodiments are expected to be useful in treatment and/or diagnostic applications relating to Alzheimer's Disease, as well as other tauopathies.

Alzheimer's disease (AD), a leading cause of dementia, develops in one percent of the population between the ages 65 and 69, and increases to 40-50% in those 95 years and older. AD patients exhibit telltale clinical symptoms that include cognitive impairment and deficits in memory function. In these patients, the presence of AD is confirmed by heavy senile plaque burden and neurofibrillary tangles (NFT) found in the cerebral cortex upon post-mortem histopathological examination. The mature senile plaques consist of extracellular 0-amyloid peptides derived from enzymatic processing of amyloid precursor protein and intracellular neurofibrillary tangles (NFT), which are derived from filaments of hyperphosphorylated tau proteins. Aggregates of hyperphosphorylated tau, such as neurofibrillary tangles, are linked to the degree of cognitive impairment in Alzheimer's disease. In AD and various other tauopathies, tau aggregates appear in specific brain regions and patterns that are linked to disease risk, onset, and or progression, and these regions and patterns are known to skilled artisans.

Cytokines regulate normal homeostatic tissue functions, and dysregulation of these cytokine networks is associated with pathological conditions. The central nervous system (CNS), where few blood-borne immune cells circulate, seems to be particularly vulnerable to dysregulated cytokine networks. In neurodegenerative diseases, CNS-resident cells are the predominant producers of pro-inflammatory cytokines and can contribute to dysregulated cytokine networks and neuroinflammation. Damage to the CNS may involve recruitment of circulating immune cells resulting in an innate immune response consisting of resident microglia, peripherally derived monocytes, macrophages and dendritic cells. The activation states of microglia and macrophages are not strictly pro or anti-inflammatory and instead may have a spectrum of functional states. Microglia and/or peripherally derived monocytes and macrophages may acquire an anti-inflammatory phenotype, in which they remove debris and promote regeneration and homeostasis. Neuronal dysfunction or damage can also activate microglia to produce pro-inflammatory cytokines and recruit leukocytes from the bloodstream. In neurodegenerative conditions, such as Alzheimer's disease (AD), microglia activation is a frequent finding and reflects the tissue response to accumulation of extracellular beta-amyloid plaques and hyperphosphorylated tau aggregates. Neuroinflammation is an important component of neurodegenerative diseases and is characterized by elevated production of pro-inflammatory cytokines by CNS cells (Becher, B., Spath, S. & Goverman, J. *Cytokine networks in neuroinflammation*. Nat Rev Immunol 17, 49-59 (2017)). Neuroinflammation and microgliosis are believed to be mechanisms underlying neurodegenerative diseases such as plaque accumulation in Alzheimer's disease, and neuronal death and dysfunction in Parkinson's disease and Huntington's disease.

Microgliosis involves the abnormal proliferation and/or hypertrophy of microglia in response to inflammatory signals. Broadly, IL-34 acts as a potent and pleiotropic cytokine in the regulation of inflammatory and immune processes and is a key regulatory cytokine for the growth of CNS-resident microglia in normal tissue homeostasis. IL-34 is expressed by neurons in the cortex, the anterior olfactory nucleus and the hippocampus. IL-34 displays low sequence homology to CSF-1, but has a similar general structure, and both cytokines bind to a common receptor CSF-1R and triggers receptor autophsphorylation and dimerization with subsequent activation of multiple signaling pathways (A. Freuchet, et al J Leukoc Biol 2021 October; 110(4):771-796). IL-34 is a secreted homodimeric cytokine that acts as one of two activating ligands for CSF1R, and triggers receptor autophosphorylation and dimerization with subsequent activation of multiple signaling pathways (See, for example, Structural basisfor the dual recognition of helical cytokines IL-34 and CSF-1 by CSF-1R. Structure 20, 676-687, and Felix J, De Munck S, Verstraete K, Meuris L, Callewaert N, Elegheert J. et al.). Human IL-34 polypeptides are disclosed for example in U.S. Pat. No. 9,770,486 and consist of 242 amino acids with the leader sequence, and 222 amino acids in mature form (SEQ ID NO: 31).

Anti-IL-34 antibodies have been described in the art, and for example, WO 2016/196679 recites various anti-IL-34 antibodies and potential uses thereof. However, to date, no antibody targeting IL-34 has been approved for therapeutic use.

Thus, there remains an unmet need for alternative and/or improved anti-IL-34 antibodies, pharmaceutical compositions thereof, and methods of using the same for therapeutic and/or in diagnostic applications relating to immune-mediated diseases involving IL-34, and/or diseases treatable with an anti-IL-34 antibody, such as neuroinflammatory disorders, and/or Alzheimer's Disease.

SUMMARY OF INVENTION

Embodiments of the present disclosure provide novel anti-human IL-34 antibodies. According to some embodiments, the present disclosure provides antibodies which comprise a light chain variable region (LCVR) and a heavy chain variable region (HCVR), wherein the LCVR comprises complementarity determining regions (CDRs) LCDR1, LCDR2 and LCDR3 and the HCVR comprises CDRs HCDR1, HCDR2 and HCDR3 are selected from the groupings of CDR combinations provided in Table 1. The sequence identifiers used herein are listed in Table 1 and throughout the specification, and the sequences are provided in the amino acid and nucleotide sequence listing provided herein.

TABLE 1

Amino Acid and Nucleotide Sequences

| Sequence | Antibody 1 |
|---|---|
| HC | SEQ ID NO: 1 |
| LC | SEQ ID NO: 2 |
| HCVR | SEQ ID NO: 3 |

TABLE 1-continued

Amino Acid and Nucleotide Sequences

| Sequence | Antibody 1 |
| --- | --- |
| LCVR | SEQ ID NO: 4 |
| HCDR1 | SEQ ID NO: 5 |
| HCDR2 | SEQ ID NO: 6 |
| HCDR3 | SEQ ID NO: 7 |
| LCDR1 | SEQ ID NO: 8 |
| LCDR2 | SEQ ID NO: 9 |
| LCDR3 | SEQ ID NO: 10 |
| DNA HC | SEQ ID NO: 11 |
| DNA LC | SEQ ID NO: 12 |

Accordingly, embodiments of the present disclosure provide an antibody that binds human IL-34 wherein the antibody comprises a heavy chain variable region (VH) and a light chain variable region (VL), wherein the VH comprises heavy chain complementarity determining regions (HCDR) HCDR1, HCDR2, and HCDR3, and the VL comprises light chain complementarity determining regions (LCDR) LCDR1, LCDR2, and LCDR3, wherein the HCDR1 comprises SEQ ID NO: 5, the HCDR2 comprises SEQ ID NO: 6, the HCDR3 comprises SEQ ID NO: 7, the LCDR1 comprises SEQ ID NO: 8, the LCDR2 comprises SEQ ID NO: 9, and the LCDR3 comprises SEQ ID NO: 10.

Accordingly, embodiments of the present disclosure also provide antibodies comprising the LCVR having the amino acid sequence of SEQ ID NO: 4 and the HCVR having the amino acid sequence of SEQ ID NO: 3.

Accordingly, embodiments of the present disclosure further provide an antibody that binds human IL-34 wherein the antibody comprises a heavy chain (HC) comprising SEQ ID NO: 1 and a light chain (LC) comprising SEQ ID NO: 2.

According to other embodiments, the present disclosure also provides antibodies comprising the LCVR having the amino acid sequence of SEQ ID NO: 4 and the HCVR having the amino acid sequence of SEQ ID NO: 3, with a hinge region and Fc region selected from SEQ ID NO: 32 and SEQ ID NO: 33.

As used herein "Antibody 1" refers to an antibody having the HCDR1 amino acid sequence of SEQ ID NO: 5, the HCDR2 amino acid sequence of SEQ ID NO: 6, the HCDR3 amino acid sequence of SEQ ID NO: 7, the LCDR1 amino acid sequence of SEQ ID NO: 8, the LCDR2 amino acid sequence of SEQ ID NO: 9, the LCDR3 amino acid sequence of SEQ ID NO: 10, the HCVR amino acid sequence of SEQ ID NO: 3, the LCVR amino acid sequence of SEQ ID NO: 4, the HC amino acid sequence of SEQ ID NO: 1, the LC amino acid sequence of SEQ ID NO: 2. Antibody 1 can be encoded by the HC DNA sequence of SEQ ID NO: 11, and the LC DNA sequence of SEQ ID NO: 12. The framework and CDR sequences in each of the antibodies for which sequences are set forth herein are annotated using annotation rules in agreement with the method of North, et al. *J. Mol. Biol.* 2011: 406: 228-256 unless otherwise specified.

According to other embodiments, the present disclosure also provides antibodies comprising a LC having an amino acid sequence with at least 95% sequence homology to SEQ ID NO: 2 and a HC having an amino acid sequence with at least 95% sequence homology to SEQ ID NO: 1.

According to other embodiments, the present disclosure also provides antibodies comprising a LC having the amino acid sequence of SEQ ID NO: 2, and a HC having the amino acid sequence of SEQ ID NO: 35, further referred to herein as Antibody 2.

According to other embodiments, the present disclosure also provides antibodies comprising a LC having the amino acid sequence of SEQ ID NO: 2, and a HC having the amino acid sequence of SEQ ID NO: 36, further referred to herein as Antibody 3.

According to other embodiments, the present disclosure also provides antibodies comprising a LC having the amino acid sequence of SEQ ID NO: 2, and a HC having the amino acid sequence of SEQ ID NO: 37, further referred to herein as Antibody 4.

The carboxy-terminal portion of each HC defines a constant region primarily responsible for effector functions, and in some embodiments of the present disclosure the antibodies have one or more modifications in the constant region of each HC that reduce effector functions. Preferably, embodiments of the present disclosure are IgG4 antibodies, and thus contain an IgG4 Fc region, or an Fc region derived from human IgG4, e.g., a modified IgG4 Fc region.

According to some embodiments, modifications in the constant region of both HCs which reduce effector functions, and amino acid substitutions are introduced into the IgG4 hinge and Fc regions. Thus, some embodiments have modifications in the constant region of both HCs which include the amino acid alanine at both residues 230 and 231 (exemplified in HC of Antibody 1, and SEQ ID NO: 33, respectively), and further modifications in the constant region of both HCs promoting stability, including the amino acid proline at residue 224 (exemplified in HC of Antibody 1, and for example in SEQ ID NO: 32), and the deletion of the amino acid lysine at residue 443 (exemplified HC of SEQ ID NO: 1).

The antibodies of the present disclosure are believed to have a combination of particularly advantageous properties over prior art anti-IL-34 antibodies, including but not limited to, one or more of the following properties: 1) desirable association and dissociation rates, 2) potency in neutralization of human IL-34 to achieve an anti-neuroinflammatory response and in vivo efficacy, 3) sufficiently potent as a monotherapy for the treatment and/or prevention of immune-mediated and/or inflammatory disorders; 4) a sustained duration of action; 5) sufficiently limited induction of undesirable cytokine release, 6) acceptably low immunogenicity (i.e., sufficiently non-immunogenic in humans); 7) avoidance of untoward immunocompromise; and/or 8) desirable in vivo stability, physical and chemical stability including, but not limited to, thermal stability, solubility, low self-association, and pharmacokinetic characteristics which are acceptable for development and/or use in the treatment of inflammatory or neuroinflammatory disorders, for example AD.

DETAILED DESCRIPTION

Embodiments of the present disclosure provide a significant advance over the prior art by providing compositions and methods useful in the prevention, downregulation, or amelioration of inflammatory and/or neuroinflammatory related disorders, through IL-34 neutralization, using a pharmacologically advantageous anti-human IL-34 antibody as provided in the embodiments described herein. Anti-human IL-34 antibodies of the present disclosure are capable of improving immune and/or inflammatory pathology, or restoring immune homeostasis, preferably, through inhibition of the innate arm of the immune response, and/or abrogation of microgliosis or other monocyte/macrophage lineage cellular activation and or proliferation, thereby directly modifying underlying disease pathology. The use of such antibodies clinically may lead to durable long-term improvement of the disease(s) being treated.

Further, there is a need for diagnostic anti-human IL-34 antibodies that are specific for human IL-34, and possess improved binding affinity, and demonstrate enhanced sensitivity in human IL-34 determinations, and improved enzyme-linked immunosorbent assay (ELISA) assay conditions that result in minimal interference and broad dilutional linearity. According to some aspects of the present disclosure, anti-human IL-34 antibodies, including human IL-34 neutralizing antibodies, are provided which bind human IL-34 given by SEQ ID NO: 31. Interleukin 34 (IL-34; also known as uncharacterized protein C16orf77) is secreted as a homodimer consisting of 39 kDa monomers. It belongs to no known cytokine family. Human IL-34 is synthesized as a 242 amino acid (AA) precursor that contains a 20 AA signal sequence, and results in a 222 AA mature chain. As used herein IL-34 refers to the mature chain. The mature chain contains one potential site of N-linked glycosylation. IL-34 is expressed in various tissues, including the heart, brain, liver, kidney, spleen, thymus, testes, ovary, small intestine, prostate, and colon, and is most abundant in the spleen. "h IL-34" or "human IL-34" when used herein in reference to an IL-34 polypeptide, unless otherwise stated, refers to wild-type human IL-34, and preferably has the amino acid sequence set forth in SEQ ID NO: 31, which is mature IL-34 having the leader sequence removed. (See, for example, Lin et. al., Science (2008) Vol. 320, Issue 5877, pp. 807-811).

An exemplary human IL-34 (SEQ ID NO: 31) has the amino acid sequence: NEPLEMWPLTQNEECTVTGF-LRDKLQYRSRLQYMKHYFPINYKISVPYEGVFRIAN-VTRLQRAQVSERELRYLWVLVSLSATESVQDVLLEG-HPSWKYLQEVETLLLNVQQGLTDVEVSPKVESVLS-LLNAPGPNLKLVRPKALLDNCFRVMELLYCSCCKQS-SVLNWQDCEVPSPQSCSPEPSLQYAATQLYPPPPWS-PSSPPHSTGSVRPVRAQGE GLLP.

As used herein, "human anti-IL34 antibody" or "anti-human IL-34 antibody" refers to an antibody that binds to human IL-34. Preferably an "human anti-IL34 antibody" or "anti-human IL-34 antibody" administered in vitro or in vivo results in an IL-34 activity-neutralizing and/or blocking response, such as at least one significantly lessened desired activity, for example a desired reduction in IL-34 signaling as evidenced by a change in an IL-34 responsive molecular or cellular endpoint. For instance, microglia number, density, or phenotype in the CNS, are examples of possible IL-34 responsive molecular or cellular effects. As used herein, the terms "signaling" and "signal transduction" and "IL-34-mediated", as they relate to IL-34, refer to cellular and/or intercellular responses which result from the activity of IL-34.

The term "antibody," as used herein, refers to an immunoglobulin molecule that binds an antigen. Embodiments of an antibody include a monoclonal antibody, polyclonal antibody, human antibody, humanized antibody, chimeric antibody or conjugated antibody. The antibodies can be of any class (e.g., IgG, IgE, IgM, IgD, IgA) and any subclass (e.g., IgG1, IgG2, IgG3, IgG4). An exemplary antibody is an immunoglobulin G (IgG) type antibody comprised of four polypeptide chains: two heavy chains (HC) and two light chains (LC) that are cross-linked via inter-chain disulfide bonds. LCs are classified as kappa or lambda, which are each characterized by a specific constant region. Embodiments of the present disclosure may comprise an IgG1, IgG2 or IgG4 antibody, and further comprise kappa light chains or lambda light chains. Preferably antibodies of the present disclosure comprise light chain constant regions which are kappa constant regions.

HCs are classified as gamma, mu, alpha, delta, or epsilon, and define the isotype of an antibody as IgG, IgM, IgA, IgD, or IgE, respectively. The amino-terminal portion of each of the four polypeptide chains includes a variable region of about 100-125 or more amino acids primarily responsible for antigen recognition. The carboxyl-terminal portion of each of the four polypeptide chains contains a constant region primarily responsible for effector functions. Each heavy chain is comprised of a heavy chain variable region (VH) and a heavy chain constant region. The constant region of the heavy chains contains CH1, CH2, and CH3 domains. CH1 comes after the HCVR; the CH1 and HCVR form the heavy chain portion of an antigen-binding (Fab) fragment, which is the part of an antibody that binds antigen(s). CH2 comes after the hinge region and before CH3. CH3 comes after CH2 and is at the carboxy-terminal end of the heavy chain. The constant region of the light chains contains one domain, CL. CL comes after the LCVR; the CL and LCVR form the light chain portion of a Fab.

The antibodies of the present disclosure include IgG HCs which can be further divided into subclasses, e.g., IgG1, IgG2, IgG3, IgG4, and embodiments of the present disclosure may include one or more modifications in the constant region of each HC, for example that enhance or reduce effector function. The term "Fc region" as used herein refers to a region of an antibody, which comprises the CH2 and CH3 domains of the antibody heavy chain. Optionally, the Fc region may include a portion of the hinge region or the entire hinge region of the antibody heavy chain. IgG1 is known to induce antibody-dependent cell cytotoxicity (ADCC) and complement-dependent cytotoxicity (CDC), and Fc mutations described herein may reduce aggregation, reduce or enhance ADCC or CDC activities, (or other functions), and/or modify the pharmacokinetics of the antibodies. Embodiments of anti-human IL-34 antibodies described herein have reduced binding to the FcγR and C1q receptors, thereby reducing or eliminating the cytotoxicity which may be induced by antibodies with wild type IgG Fc regions. Thus, according to some embodiments, mutations are introduced in the Fc region at positions as described herein. Patient safety can be improved with sufficiently reduced or eliminated effector functions of such anti-human IL-34 antibodies comprising a modified Fc region, and in combination with other properties described herein, provide therapeutic agents with an improved profile of useful activities while avoiding undesirable activities.

When expressed in certain biological systems, antibodies are glycosylated in the Fc region. Typically, glycosylation occurs in the Fc region of the antibody at a highly conserved N-glycosylation site. N-glycans typically attach to asparagine. Antibodies may be glycosylated at other positions as well. Antibodies of the present disclosure are monoclonal antibodies. Monoclonal antibodies are antibodies derived from a single copy or clone including, for example, any eukaryotic, prokaryotic or phage clone, and not defined by the method by which it is produced. Monoclonal antibodies can be produced, for example, by hybridoma technologies, recombinant technologies, phage display technologies, synthetic technologies, e.g., CDR-grafting, or combinations of such or other technologies known in the art. The present disclosure contemplates the antibodies of the present disclosure are human or humanized antibodies. In the context of monoclonal antibodies, the terms "human" and "humanized" are well-known to those of ordinary skill in the art (Weiner L J, J. Immunother. 2006; 29: 1-9; Mallbris L, et al., J. Clin. Aesthet. Dermatol. 2016; 9: 13-15). Exemplary embodiments of antibodies of the present disclosure also include antibody fragments or antigen-binding fragments, which comprise at least a portion of an antibody retaining the ability to specifically interact with an antigen such as Fab, Fab', F(ab')2, Fv fragments, scFv antibody fragments, disulfide-linked Fvs (sdFv), a Fd fragment and linear antibodies.

available on at www.imgt.org; see Lefranc et al., Nucleic Acids Res. 1999; 27:209-212).

For the purposes of the present disclosure, and except where specified otherwise, the North CDR definitions are used for the anti-IL-34 antibodies described herein, and assignment of amino acids to CDR domains within the LCVR and HCVR regions. Below Table 2 provides CDR sequences for Antibody 1, and/or Antibodies of the present disclosure, based on conventions of North, Kabat, Chothia, and/or IMGT respectively, generated using Benchling informatics software.

TABLE 2

Exemplary CDRs of Antibody 1 (or Antibodies of the present disclosure)

| Ab | HCDR1 | HCDR2 | HCDR3 | LCDR1 | LCDR2 | LCDR3 |
|---|---|---|---|---|---|---|
| North | AASGFA FSNYAM S (SEQ ID NO: 5) | AISASGGKT Y (SEQ ID NO: 6) | AKRGYLW HAFDH (SEQ ID NO: 7) | RASQSVSSL YLA (SEQ ID NO: 8) | YGASSRAT (SEQ ID NO: 9) | QVVGSSP PFT (SEQ ID NO: 10) |
| Kabat | NYAMS (SEQ ID NO: 13) | AISASGGK TYYADSVK G (SEQ ID NO: 14) | RGYLWHA FDH (SEQ ID NO: 15) | RASQSVSS LYLA (SEQ ID NO: 16) | GASSRAT (SEQ ID NO: 17) | QVVGSS PPFT (SEQ ID NO: 18) |
| Chothia | GFAFSN Y (SEQ ID NO: 19) | SASGGK (SEQ ID NO: 20) | RGYLWHA FDH (SEQ ID NO: 21) | RASQSVSS LYLA (SEQ ID NO: 22) | GASSRAT (SEQ ID NO: 23) | QVVGSS PPFT (SEQ ID NO: 24) |
| IMGT | GFAFSN YA (SEQ ID NO: 25) | ISASGGKT (SEQ ID NO: 26) | AKRGYLW HAFDH (SEQ ID NO: 27) | QSVSSLY (SEQ ID NO: 28) | GAS (SEQ ID NO: 29) | QVVGSS PPFT (SEQ ID NO: 30) |

The amino terminal portion of each LC and HC includes a variable region of about 100-120 amino acids primarily responsible for antigen recognition via the CDRs contained therein. The VH and VL regions can be further subdivided into regions of hyper-variability, termed complementarity determining regions (CDRs), interspersed with regions that are more conserved, termed framework regions (FR). The CDRs are exposed on the surface of the protein and are important regions of the antibody for antigen binding specificity. Each VH and VL is composed of three CDRs and four FRs, arranged from amino-terminus to carboxyl-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues that form specific interactions with the antigen. The functional ability of an antibody to bind a specific antigen is largely influenced by the six CDRs. Assignment of amino acid residues to the CDRs may be done according to the well-known schemes, including those described in Kabat (Kabat et al., "Sequences of Proteins of Immunological Interest," National Institutes of Health, Bethesda, Md. (1991)), Chothia (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)), North (North et al., "A New Clustering of Antibody CDR Loop Conformations", Journal of Molecular Biology, 406, 228-256 (2011)), or IMGT (the international ImMunoGeneTics database Antibody embodiments of the present disclosure possess a combination of pharmacologically useful and important activities and properties, and in one respect are capable of binding with high affinity and high specificity to human IL-34, as well as other useful properties. The terms "bind" and "binds" as used herein are intended to mean, unless indicated otherwise, the ability of a protein or molecule to form attractive interactions with another protein or molecule, which results in proximity of the two proteins or molecules as determined by common methods known in the art. The phrase "specifically binds", as used herein in reference to the affinity of an anti-IL-34 antibody for human IL-34, is intended to mean, unless indicated otherwise, a $K_D$ of preferably less than about $1 \times 10^{-10}$ M, even more preferably, between about $1 \times 10^{-10}$ M and about $1 \times 10^{-12}$ M, as determined by common methods known in the art, including by use of a SPR (Surface Plasmon Resonance) biosensor, and/or solution equilibrium titration (SET) measured by MSD (Meso Scale Discovery) instrument, essentially as described herein. The phrase "specifically binds" also indicates the relative affinity of an anti-IL-34 antibody for human IL-34, as compared to other antigens, wherein the affinity for human IL-34 results in a specific recognition of human IL-34.

Antibody embodiments of the present disclosure may be expressed and produced by a variety of techniques known in the art from constructs comprising sequences of the present embodiments. The terms "nucleic acid" or "polynucleotide", as used interchangeably herein, refer to polymers of nucleotides, including single-stranded and/or double-stranded nucleotide-containing molecules, such as DNA, cDNA and RNA molecules, incorporating native, modified, and/or analogs of, nucleotides. Polynucleotides of the present disclosure may also include substrates incorporated therein, for example, by DNA or RNA polymerase or a synthetic reaction. A DNA molecule of the present disclosure is a DNA molecule that comprises a non-naturally occurring polynucleotide sequence encoding a polypeptide having the amino acid sequence of at least one of the polypeptides in an antibody of the present disclosure (e.g., heavy chain, light chain, variable heavy chain, and variable light chain).

An isolated DNA encoding a HCVR or LCVR region can be converted to a full-length heavy chain gene by operably linking the respective HCVR or LCVR-encoding DNA to another DNA molecule encoding heavy or light chain constant regions, to form a heavy or light chain respectively. The sequences of human, as well as other mammalian, heavy chain constant region genes are known in the art. DNA fragments encompassing these regions can be obtained, e.g., by standard PCR amplification.

The polynucleotides of the present disclosure can be expressed in a host cell after the sequences have been operably linked to an expression control sequence. The expression vectors are typically replicable in the host organisms either as episomes, or as an integral part of the host chromosomal DNA. Commonly, expression vectors will contain selection markers, e.g., tetracycline, neomycin, and dihydrofolate reductase, to permit detection of those cells transformed with the desired DNA sequences. The vectors containing the polynucleotide sequences of interest (e.g., the polynucleotides encoding the polypeptides of the antibody and expression control sequences) can be transferred into the host cell by well-known methods, which vary depending on the type of cellular host.

The antibodies of the present disclosure can readily be produced in mammalian cells, non-limiting examples of which includes CHO, NS0, HEK293 or COS cells. The host cells are cultured using techniques well known in the art. Mammalian expression of antibodies typically results in glycosylation. Glycosylation of antibodies is typically either N-linked or O-linked. N-linked glycosylation refers to the attachment of a carbohydrate moiety to the side chain of an asparagine residue. O-linked glycosylation refers to the attachment of a sugar, for example N-acetylgalactosamine, galactose, or xylose to a hydroxyamino acid. Typically, glycosylation occurs in the Fc region of the antibody at a highly conserved N-glycosylation site (e.g., position 297 in IgG1, according to IMGT or EU Index numbering). Glycosylation sites can be modified to alter glycosylation (e.g., blocking or reducing glycosylation or altering the amino acid sequence to produce additional or diverse glycosylation).

Mammalian expression of antibodies from IgG subclasses can result in clipping of C-terminal amino acids from one or both heavy chains; for example, one or two C-terminal amino acids can be removed for IgG1 antibodies. For IgG1 antibodies, if a C-terminal lysine is present, then it may be truncated or clipped off from the heavy chain during expression. Additionally, a penultimate glycine may also be truncated or clipped off from the heavy chain as well.

Mammalian expression of antibodies can also result in the modification of N-terminal amino acids. For example, where the N-terminal most amino acid of a heavy chain or light chain is a glutamine, it may be modified into pyro-glutamic acid.

An antibody of the present disclosure, or a pharmaceutical composition comprising the same, may be administered by parenteral routes, non-limiting examples of which are subcutaneous administration and intravenous administration.

An antibody of the present disclosure may be administered to a patient with pharmaceutically acceptable carriers, diluents, or excipients in single or multiple doses. Pharmaceutical compositions of the present disclosure can be prepared by methods well known in the art (e.g., Remington: The Science and Practice of Pharmacy, 22nd ed. (2012), A. Loyd et al., Pharmaceutical Press) and comprise an antibody, as disclosed herein, and one or more pharmaceutically acceptable carriers, diluents, or excipients.

Uses of Antibody Embodiments of the Present Invention:

According to some embodiments, the anti-IL-34 antibodies of the present disclosure are useful in the treatment of immune-mediated diseases. As used herein, the term "immune-mediated disease" or "inflammatory disease or disorder" are used interchangeably and refer to undesirable conditions that arise from an inappropriate, or excessive immune responses in which IL-34 inhibition results in more homeostatic and less pathological responses. The term "immune-mediated disease" or "inflammatory disorder" is meant to include such conditions, whether they be mediated by microglia or macrophage cellular immune responses, or those of similar tissue-resident cell types, such as histiocytes, Kupffer cells, alveolar macrophages, intestinal macrophages, macrophage-like synoviocytes, or Langerhans cells. Exemplary diseases contemplated to be treated by the antibodies of the disclosure described herein include Alzheimer's Disease; a Tauopathy disease; Sjogren's syndrome (SS); Rheumatoid arthritis (RA); inflammatory bowel disease (IBD), atopic dermatitis, kidney disease, sepsis, Amyotrophic Lateral Sclerosis (ALS), and/or non-alcoholic fatty liver disease (NAFLD).

In some more specific embodiments, the immune-mediated disease is Alzheimer's Disease (AD). According to other embodiments of the present disclosure, the anti-IL-34 antibodies are useful in diagnostic applications for immune-mediated diseases. In some embodiments, the immune-mediated diseases are at least one of AD; Sjogren's syndrome (SS); Rheumatoid arthritis (RA); inflammatory bowel disease (IBD), atopic dermatitis, kidney disease, sepsis, and/or non-alcoholic fatty liver disease (NAFLD).

The present disclosure further provides pharmaceutical compositions comprising an anti-IL-34 antibody of the present disclosure and one or more pharmaceutically acceptable carriers, diluents or excipients. Further, the present disclosure provides a method of treating an immune-mediated disease, such as AD; Sjogren's syndrome (SS); Rheumatoid arthritis (RA); inflammatory bowel disease (IBD), atopic dermatitis, kidney disease, sepsis, and/or non-alcoholic fatty liver disease (NAFLD), comprising administering to a patient in need thereof a pharmaceutical composition of the present disclosure.

In addition, the present disclosure provides a method of treating immune-mediated diseases. More particularly, the present disclosure provides a method of treating immune-mediated diseases, including AD; Sjogren's syndrome (SS); Rheumatoid arthritis (RA); inflammatory bowel disease (IBD), atopic dermatitis, kidney disease, sepsis, and/or non-alcoholic fatty liver disease (NAFLD), comprising administering to a patient in need thereof an effective amount of an anti-IL-34 antibody of the present disclosure.

The present disclosure also provides an anti-IL-34 antibody of the present disclosure for use in therapy. More particularly, the present disclosure provides an anti-IL-34 antibody of the present disclosure for use in treatment of immune-mediated diseases including AD; Sjogren's syndrome (SS); Rheumatoid arthritis (RA); inflammatory bowel disease (IBD), atopic dermatitis, kidney disease, sepsis, and/or non-alcoholic fatty liver disease (NAFLD).

In certain embodiments, the present disclosure provides the use of an anti-IL-34 antibody of the present disclosure in the manufacture of a medicament for the treatment of one or more immune-mediated diseases including AD; Sjogren's syndrome (SS); Rheumatoid arthritis (RA); inflammatory bowel disease (IBD), atopic dermatitis, kidney disease, sepsis, and/or non-alcoholic fatty liver disease (NAFLD).

Antibodies of the present disclosure are useful in the identification of immune-mediated disorders wherein IL-34 may contribute to the etiopathogenesis of the disorder. In further embodiments, the present disclosure provides a method of treating an immune-mediated disease in a patient. Such methods comprise the steps of contacting a patient sample with an anti-IL-34 antibody and detecting binding between human IL-34 in the patient sample and the antibody; and diagnosing the patient as having; at risk for; in need of treatment for; and/or at risk of symptoms relating to an immune-mediated disease when the presence of IL-34 in the patient sample is detected as above a reference value observed in non-diseased individuals (See for example Xie, H. H., et al. *Elevated Serum Interleukin-34 Level in Patients with Systemic Lupus Erythematosus Is Associated with Disease Activity*. Sci Rep 8, 3462 (2018). According to some more specific embodiments of the methods of treating provided herein, such methods further include the steps of determining the reference value including the further steps of contacting a control standard with a first antibody which binds the same first epitope region of IL-34 as used in contacting the patient sample; contacting the control standard with a second antibody having a detectable label and which binds the same second epitope region of IL-34 as used in contacting the patient sample; and detecting a signal provided by the detectable signal. In some specific embodiments, the anti-IL-34 antibody comprises a combination of LC and HC CDRs provided in Table 1. In further embodiments, the second antibody comprises a combination of LCVR and HCVR provided in Table 1. According to some embodiments, the reference value is approximately 10-30 pg/mL, for example from CNS tissue lysates. In certain embodiments, the immune-mediated disease is one of AD; Sjogren's syndrome (SS); Rheumatoid arthritis (RA); inflammatory bowel disease (IBD), atopic dermatitis, kidney disease, sepsis, and/or non-alcoholic fatty liver disease (NAFLD). In some embodiments, the patient sample is one of CSF, blood, serum, a tissue lysate, or plasma. According to some embodiments, the method further includes the steps of contacting the patient sample with a second anti-IL-34 antibody which binds a second epitope region of IL-34, and has a detectable label, and detecting a signal provided by the detectable signal. In further embodiments, the second antibody comprises a combination of LC and HC CDRs provided in Table 1. In further embodiments, the second antibody comprises a combination of LCVR and HCVR provided in Table 1. According to certain embodiments, the first and second anti-IL-34 antibodies do not bin together.

According to some embodiments, the present disclosure provides a method of detecting IL-34 in a patient sample comprising the steps of contacting the patient sample with a first antibody which binds a first epitope region of IL-34; contacting the patient sample with a second antibody which binds a second epitope region of IL-34 and has a detectable label; and detecting a signal provided by said detectable label. In some embodiments, the patient sample is one of blood, serum, a tissue lysate or plasma. According to some more specific embodiments, the first epitope region of IL-34 partially overlaps with the second epitope region of IL-34. Further, in some embodiments, said steps of contacting with the first and second antibodies occurs simultaneously. In some specific embodiments, the first antibody comprises a combination of LC and HC CDRs provided in Table 1. In further embodiments, the first antibody comprises a combination of LCVR and HCVR provided in Table 1.

According to some embodiments of the present disclosure, a method of quantifying IL-34 in a patient sample is provided. Such method includes the steps of contacting the patient sample with a first antibody which binds a first epitope region of IL-34; contacting the patient sample with a second antibody which binds a second epitope region of IL-34 and said has a detectable label; and detecting the signal provided by said detectable label; contacting a control standard with a first antibody which binds the same first epitope region of IL-34 (as used in contacting the patient sample); contacting the control standard with a second antibody which binds the same second epitope region of IL-34 (as used in contacting the patient sample) and having a detectable label; and detecting a signal provided by said detectable signal. In some embodiments, the patient sample is one of blood, serum or plasma, or a tissue lysate. According to some more specific embodiments, the first epitope region of IL-34 partially overlaps with the second epitope region of IL-34. Further, in some embodiments, said steps of contacting with the first and second antibodies occurs simultaneously. In some specific embodiments, the first antibody comprises a combination of LC and HC CDRs provided in Table 1. In further embodiments, the first antibody comprises a combination of LCVR and HCVR provided in Table 1. In some specific embodiments, the second antibody comprises a combination of LC and HC CDRs provided in Table 1 or herein. In further embodiments, the second antibody comprises a combination of LCVR and HCVR provided in Table 1.

According to some embodiments, a method of diagnosing an immune-mediated disease is provided. Such method comprises the steps of contacting a patient sample with an anti-IL-34 antibody and detecting binding between IL-34 in the patient sample and the antibody. According to some specific embodiments, the method of diagnosing includes diagnosing the patient as having; at risk for; in need of treatment for; and/or at risk of symptoms relating to an immune-mediated disease when the presence of IL-34 in the patient sample is detected as above a reference value. According to some more specific embodiments, such methods further include the steps of determining the reference value including the steps of contacting a control standard with a first antibody which binds the same first epitope region of IL-34 as used in contacting the patient sample; contacting the control standard with a second antibody having a detectable label and which binds the same second epitope region of IL-34 as used in contacting the patient sample; and detecting a signal provided by the detectable signal. In some embodiments, the first antibody comprises a combination of LC and HC CDRs provided in Tables 1. Some embodiments of the method of diagnosing an immune-mediated disease, provided herein, further includes the steps of contacting the patient sample with a second anti-IL-34 antibody which binds a second epitope region of IL-34 and has a detectable label; and detecting a signal provided by the detectable label. In some specific embodiments, the anti-IL-34 antibody comprises a combination of LC and HC CDRs provided in Table 1. In further embodiments, the antibody comprises a combination of LCVR and HCVR provided in Table 1. According to specific embodiments, the first epitope region of IL-34 partially overlaps with the second epitope region of IL-34. According to certain embodiments, the first and second antibodies do not bin together. According to further embodiments, the reference value is approximately a range from 10-30 pg/mL from CNS tissue lysates, and/or as determined by the skilled artisan for the appropriate reference group and sample source. In further embodiments, the immune-mediated disease is one of AD; a tauopathy; Sjogren's syndrome (SS); Rheumatoid arthritis (RA); inflammatory bowel disease (IBD), atopic dermatitis, kidney disease, sepsis, and/or non-alcoholic fatty liver disease (NAFLD).

In an embodiment the present disclosure provides a method of determining the human IL-34 level in a bodily fluid comprising: (a) contacting the bodily fluid with an anti-human IL-34 diagnostic monoclonal antibody, or antigen-binding fragment thereof, that specifically binds to human IL-34 consisting of the amino acid sequence as in SEQ ID NO: 31, the antibody, or antigen-binding fragment thereof, comprising: light chain complementarity determining regions LCDR1, LCDR2, and LCDR3 comprising the amino acid sequences (SEQ ID NO: 8), (SEQ ID NO: 9), and (SEQ ID NO: 10), respectively, and heavy chain complementarity determining regions HCDR1, HCDR2, and HCDR3 comprising the amino acid sequences (SEQ ID NO: 5), (SEQ ID NO: 6), and (SEQ ID NO: 7), respectively; (b) optionally, removing any non-specifically bound monoclonal antibody or, antigen-binding fragment thereof, and (c) detecting and/or quantifying the amount of monoclonal antibody, or antigen-binding fragment thereof, which is specifically bound to human IL-34. Preferably, wherein said bodily fluid is blood, serum or plasma, or cerebrospinal fluid, and said contacting occurs ex vivo.

Tauopathy diseases include but are not limited to, Alzheimer's disease (AD), Pick's disease (PiD), progressive supranuclear palsy (PSP), corticobasal degeneration (CBD), argyrophilic grain disease, Down's Syndrome, chronic traumatic encephalopathy (CTE), traumatic brain injury (TBI), frontotemporal dementia with Parkinsonism linked to chromosome 17 (FTDP-17), Parkinsonism-dementia complex of Guam, Niemann-Pick disease type C, myotonic dystrophy (See Li, C., Götz, J. *Tau-based therapies in neurodegeneration: opportunities and challenges*. Nat Rev Drug Discov 16, 863-883 (2017)).

In embodiments of the disclosure a patient is a human who has been diagnosed as having a medical risk, condition or disorder, such as one of the diseases or disorders described herein, in need of treatment with an antibody described herein. In those instances where the disorders which can be treated by the methods of the present disclosure are known by established and accepted classifications, such as Alzheimer's Disease; a tauopathy disease; Sjogren's syndrome (SS); Rheumatoid arthritis (RA); inflammatory bowel disease (IBD), atopic dermatitis, kidney disease, sepsis, and/or non-alcoholic fatty liver disease (NAFLD), their classifications can be found in various well-known medical texts. For example, at present, the 5th edition of the Diagnostic and Statistical Manual of Mental Disorders (DSM-5), provides a diagnostic tool for identifying certain disorders described herein. Also, the International Classification of Diseases, Tenth Revision (ICD-10), provides classifications for certain disorders described herein. The skilled artisan will recognize that there are alternative nomenclatures, nosologies, and classification systems for diseases and disorders described herein, including those as described in the DSM-5 and ICD-10, and that terminology and classification systems evolve with medical scientific progress.

The term "treating" (or "treat" or "treatment") refers to slowing, interrupting, arresting, alleviating, stopping, reducing, or reversing the progression or severity of an existing symptom, disorder, condition, or disease in a subject. The term "subject" refers to a human. The terms "human subject" and "patient" are used interchangeably in the present disclosure.

As used herein, "methods of treatment" are equally applicable to use of a composition for treating the diseases or disorders described herein and/or compositions for use and/or uses in the manufacture of a medicaments for treating the diseases or disorders described herein.

The term "preventing" or "prevention" means prophylactic administration of the antibody of the present disclosure to an asymptomatic subject or a subject with pre-clinical Alzheimer's disease to prevent onset or progression of the disease.

The term "retarding the progression of" as used herein means delaying or holding back the progression of a disease or symptom thereof in a subject.

The terms "disease characterized by deposition of Aβ" or a "disease characterized by Aβ deposits" are used interchangeably and refer to a disease that is pathologically characterized by Aβ deposits in the brain or in brain vasculature. This includes diseases such as Alzheimer's disease, Down's syndrome, and cerebral amyloid angiopathy. A clinical diagnosis, staging or progression of Alzheimer's disease can be readily determined by the attending diagnostician or health care professional, as one skilled in the art, by using known techniques and by observing results. This generally includes brain plaque imaging, mental or cognitive assessment (e.g., Clinical Dementia Rating—summary of boxes (CDR-SB), Mini-Mental State Exam (MMSE) or Alzheimer's Disease Assessment Scale-Cognitive (ADAS-Cog)) or functional assessment (e.g., Alzheimer's Disease Cooperative Study-Activities of Daily Living (ADCS-ADL). The cognitive and functional assessment can be used to determine changes in a patient's cognition (e.g., cognitive decline) and function (e.g., functional decline). Accordingly, a subject may be determined to have a "slow progressing" cognitive decline according to a technique as described herein. In an exemplary embodiment, a "slow progressing" cognitive decline may be identified by iADRS wherein a subject's iADRs has declined by less than about 20, for example over a given period of time (e.g., 6, 12, 18 or 24 months). In another exemplary embodiment, a "slow progressing" cognitive decline may be identified by APOE-4 genotyping wherein a subject is APOE-4 homozygous negative r APOE-4 heterozygous. In another exemplary embodiment, a "slow progressing" cognitive decline may be identified by MMSE, wherein the subject has been determined to have a MMSE of about 27 or a MMSE decline of less than about 3 over a given period of time (e.g., 6, 12, 18 or 24 months). "Clinical Alzheimer's disease" as used herein is a diagnosed stage of Alzheimer's disease. It includes conditions diagnosed as prodromal Alzheimer's disease, mild Alzheimer's disease, moderate Alzheimer's disease, and severe Alzheimer's disease. The term "pre-clinical Alzheimer's disease" is a stage that precedes clinical Alzheimer's disease, where measurable changes in biomarkers (such as CSF Aβ42 levels or deposited brain plaque by amyloid PET) indicate the earliest signs of a patient with Alzheimer's pathology, progressing to clinical Alzheimer's disease. This is usually before symptoms such as memory loss and confusion are noticeable. Pre-clinical Alzheimer's disease also includes pre-symptomatic autosomal dominant carriers, as well as patients with higher risk for developing AD by virtue of carrying one or two APOE e4 alleles.

A reduction or slowing of cognitive decline can be measured by cognitive assessments such as Clinical Dementia Rating—summary of boxes, Mini-Mental State Exam or Alzheimer's Disease Assessment Scale-Cognitive. A reduction or slowing of functional decline can be measured by functional assessments such as ADCS-ADL.

As used herein, "mg/kg" means an amount, in milligrams, of antibody or drug administered to a subject based on his or her bodyweight in kilograms. A dose is given at one time. For example, a 10 mg/kg dose of antibody for a subject weighing 70 kg would be a single 700 mg dose of antibody given in a single administration. Similarly, a 20 mg/kg dose of antibody for a subject weighing 70 kg would be a 1400 mg dose of antibody given at a single administration.

As used herein, a human subject has "very low tau" burden if the tau burden is less than 1.10 SUVr (<1.10 SUVr) using $^{18}$F-flortaucipir based quantitative analysis where quantitative analysis refers to calculation of SUVr and SUVr represents counts within a specific target region of interest in the brain (multiblock barycentric discriminant analysis or MUBADA, see Devous et al, "Test-Retest Reproducibility for the Tau PET Imaging Agent Flortaucipir F18,"*J. Nucl. Med* 59:937-943 (2018)) when compared with a reference region (parametric estimate of reference signal intensity or PERSI, see, Southekal et al., "Flortaucipir F 18 Quantitation Using Parametric Estimation of Reference Signal Intensity," J. Nucl. Med 59:944-951 (2018)). As used herein, a human subject has "very low tau to moderate tau" burden if the tau burden is less than or equal to 1.46 SUVr (i.e., ≤1.46 SUVr) using 18F-flortaucipir based quantitative analysis where quantitative analysis refers to calculation of SUVr and SUVr represents counts within a specific target region of interest in the brain (IUBADA, see Devous et al, "Test-Retest Reproducibility for the Tau PET Imaging Agent Flortaucipir F18,"*J. Nucl. Med* 59:937-943 (2018)) when compared with a reference region (PERSI, see, Southekal et al., "Flortaucipir F 18 Quantitation Using Parametric Estimation of Reference Signal Intensity,"*J Nucl. Med* 59:944-951 (2018)).

As used herein, a human subject has "low tau to moderate tau" burden if the tau burden is from greater than or equal to 1.10 to less than or equal to 1.46 (i.e., ≤1.10 SUVr to ≤1.46 SUVr) using $^{18}$F-flortaucipir based quantitative analysis where quantitative analysis refers to calculation of SUVr and SUVr represents counts within a specific target region of interest in the brain (MUBADA, see Devous et al, "Test-Retest Reproducibility for the Tau PET Imaging Agent Flortaucipir F18,"*J. Nucl. Med* 59:937-943 (2018)) when compared with a reference region (PERSI, see, Southekal et al., "Flortaucipir F 18 Quantitation Using Parametric Estimation of Reference Signal Intensity," J. Nucl. Med. 59:944-951 (2018)). A human subject having "low tau to moderate tau" burden can also be referred to as having "intermediate" tau burden.

As used herein, a human subject has "high tau" burden if the tau burden is greater than 1.46 SUVr (i.e., >1.46 SUVr) using $^{18}$F-flortaucipir based quantitative analysis where quantitative analysis refers to calculation of SUVr and SUVr represents counts within a specific target region of interest in the brain (MUBADA, see Devous et al, "Test-Retest Reproducibility for the Tau PET Imaging Agent Flortaucipir F18,"*J. Nucl. Med.* 59:937-943 (2018)) when compared with a reference region (PERSI, see, Southekal et al., "Flortaucipir F 18 Quantitation Using Parametric Estimation of Reference Signal Intensity,"*J Nucl. Med.* 59:944-951 (2018)).

As used herein, the term "about" means up to ±10%.

As used herein, the term "innate immunity" includes the arm of the immune response which, in contrast to the adaptive arm of the immune response, is required to initiate and maintain an adaptive immune response (antibody and T cell responses).

"Effective amount" means the amount of an anti-human IL-34 antibody of the present disclosure, or a pharmaceutical composition comprising such an antibody, that will elicit the biological or medical response of or desired therapeutic effect on a tissue, system, or human, that is being sought by the treating health professional. As used herein, the term "effective response" of a patient or a patient's responsiveness to treatment refers to the clinical or therapeutic benefit imparted to a patient upon administration an antibody of the present disclosure. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects. Such benefit includes any one or more of: a decreased level of inflammation or immune activation, stabilized immune-mediated disease or disorder; or improving signs or symptoms of an immune-mediated disorder. Alternatively, such benefit includes any one or more of the following: an increased immune tolerance of transplanted organs; stabilized autoimmune disease or disorder; or improving signs or symptoms of an autoimmune disorder.

A potential advantage of methods disclosed herein is the possibility of producing marked and/or prolonged relief in a patient suffering from an immune-mediated disorder, or neuroinflammatory disorder, with an acceptable safety profile including acceptable tolerability, toxicities and/or adverse events, so that the patient benefits from the treatment method overall. The efficacy of the treatment of the present disclosure can be measured by various endpoints that are commonly used in evaluating treatments for various immune-mediated disorders. Other approaches to determining efficacy of any particular therapy of the present disclosure can be optionally employed, including, for example, immune cell activation markers, measures of inflammation, cell-cycle dependent biomarker measurement and visualization, and/or measurement of response through various inflammation or immune or tissue specific biomarker assessments.

An effective amount can be readily determined by one skilled in the art, using known techniques, and by observing results obtained under analogous circumstances. An effective amount of an anti-human IL-34 antibody of the present disclosure may be administered in a single dose or in multiple doses. Furthermore, an effective amount of an antibody of the disclosure may be administered in multiple doses of amounts that would be less than an effective amount if not administered more than once. In determining the effective amount for a patient, a number of factors are considered by the attending medical practitioner, including, but not limited to: the patient's size (e.g., weight or mass), body surface area, age, and general health; the specific disease or disorder involved; the degree of, or involvement, or the severity of the disease or disorder; the response of the individual patient; the particular compound administered; the mode of administration; the bioavailability characteristics of the preparation administered; the dose regimen selected; the use of concomitant medication; and other relevant circumstances known to medical practitioners.

A weekly, every two week, monthly, or quarterly parenteral (including, but not limited to, subcutaneous, intramuscular, and/or intravenous) dose can be from about 0.5 mg/kg to about 50 mg/kg. As used herein, the term 'month' or derivatives thereof, refers to a time period that includes 28 to 31 consecutive days.

A potential advantage of methods disclosed herein is the possibility of producing marked and/or prolonged relief in a patient suffering from an immune-mediated disorder, or neuroinflammatory disorder, with an acceptable safety profile including acceptable tolerability, toxicities and/or adverse events, so that the patient benefits from the treatment method overall, and more particularly the antibodies of the present disclosure will provide effective treatment while avoiding clinically undesirable immunosuppression and/or immune associated adverse events such as "cytokine storm" or significant cytokine release. Antibodies of the present disclosure may be useful for the treatment of cytokine storm, or otherwise adverse cytokine release. As used herein, "significant cytokine release" refers to a significant increase in measurable cytokines that can be detected by methods known to persons of ordinary skill. For example, significant cytokine release may be detected in human blood samples by ELISA, wherein cytokine levels from unstimulated blood are compared to cytokine levels with blood incubated with antibody. In some such studies, for example, a significant cytokine release may be detected if the levels of IL-6, or IL-8, or IFN-7 are at least three-fold higher in blood incubated with antibody compared to levels in unstimulated blood. Preferably, treatment of an immune-mediated disorder as described in the embodiments herein will occur wherein the patient will not experience significant cytokine release.

Combination Uses of Antibodies of the Present Disclosure:

The present disclosure further provides simultaneous, separate, or sequential combinations of an antibody of the present disclosure, in particular Antibody 1, and anti-N3pGlu Aβ antibodies, and to methods of using the combinations to treat diseases characterized by deposition of amyloid beta (Aβ), such as AD. Some known anti-Aβ antibodies useful for the present combinations include donanemab, bapineuzumab, gantenerumab, aducanumab, GSK933776, solanezumab, crenezumab, ponezumab, and lecanemab (BAN2401). The present disclosure further provides simultaneous, separate, or sequential combinations of Antibody 1 and donanemab (CAS number 1931944-80-7, SEQ ID NO's: 38 and 39), and methods of using the combinations to treat diseases characterized by deposition of amyloid beta (Aβ), such as AD (Donanemab in early Alzheimer's disease, Mintun, M. A. et al, New England Journal of Medicine (2021), 384(18), 1691-1704). Preferably the combination provides use of Antibody 1 sequentially following a course of treatment with donanemab.

As used herein, "anti-N3pGlu Aβ antibody," "anti-N3pG antibody," or "anti-N3pE antibody," used interchangeably, refer to an antibody that binds preferentially to N3pGlu Aβ over Aβ1-40 or Aβ1-42. One of ordinary skill in the art will appreciate and recognize that "anti-N3pGlu Aβ antibody", and several specific antibodies, including, "hE8L", "B12L" and "R17L" are identified and disclosed (along with methods for making and using such antibodies) in U.S. Pat. No. 8,679,498 B2 (which is hereby incorporated by reference in its entirety). See, for example, Table 1 of U.S. Pat. No. 8,679,498 B2. Each of the antibodies disclosed in U.S. Pat. No. 8,679,498 B2, including "hE8L", "B12L" and "R17L" antibodies, may be used as the anti-N3pGlu Aβ antibody of the present disclosure or in place of the anti-N3pGlu Aβ antibodies described in various aspects of the present invention. An anti-N3pGlu Aβ antibody of the present combination methods is the antibody comprising the HC and LC of SEQ ID NO's: 40 and 41, respectively.

Other representative species of an anti-N3pGlu Aβ antibody include, but are not limited to, antibodies disclosed U.S. Pat. Nos. 8,961,972; 10,647,759; 9,944,696; WO 2010/009987A2; WO 2011/151076A2; WO 2012/136552A1 and equivalents thereto, e.g., under 35 U.S.C 112(f).

One of ordinary skill in the art will appreciate and recognize that "anti-N3pGlu Aβ antibody", and several specific antibodies are identified and disclosed (along with methods for making and using such antibodies) in U.S. Pat. No. 8,961,972 (which is hereby incorporated by reference in its entirety); U.S. Pat. No. 10,647,759 (which is hereby incorporated by reference in its entirety); and U.S. Pat. No. 9,944,696 (which is hereby incorporated by reference in its entirety). Any of the anti-N3pGlu Aβ antibodies disclosed in the U.S. Pat. Nos. 8,961,972; 9,944,696; and 10,647,759 may be used as the anti-N3pGlu Aβ antibody of the present disclosure or in place of the anti-N3pGlu Aβ antibodies described in various aspects of the present invention.

One of ordinary skill in the art will appreciate and recognize that "anti-N3pGlu Aβ antibody", and several specific antibodies, including, "Antibody VI", "Antibody VII", "Antibody VIII", and "Antibody IX" are identified and disclosed (along with methods for making and using such antibodies) in WO2010/009987A2 (which is hereby incorporated by reference in its entirety). Each of these four antibodies (e.g., "Antibody VI", "Antibody VII", "Antibody VIII", and "Antibody IX") may be used as the anti-N3pGlu Aβ antibody of the present disclosure or in place of the anti-N3pGlu Aβ antibodies described in various aspects of the present invention.

One of ordinary skill in the art will appreciate and recognize that "anti-N3pGlu Aβ antibody", and several specific antibodies, including, "Antibody X" and "Antibody XI" are identified and disclosed (along with methods for making and using such antibodies) in WO 2011/151076A2 (which is hereby incorporated by reference in its entirety). Each of these two antibodies (e.g., "Antibody X" and "Antibody XI") may be used as the anti-N3pGlu Aβ antibody of the present disclosure or in place of the anti-N3pGlu Aβ antibodies described in various aspects of the present invention.

One of ordinary skill in the art will appreciate and recognize that "anti-N3pGlu Aβ antibody", and several specific antibodies, including, "Antibody XII" and "Antibody XIII" are identified and disclosed (along with methods for making and using said antibodies) in WO 2012/136552A1 (which is hereby incorporated by reference in its entirety). Each of these two antibodies (e.g., "Antibody XII" and "Antibody XIII") may be used as the anti-N3pGlu Aβ antibody of the present disclosure or in place of the anti-N3pGlu Aβ antibodies described in various aspects of the present disclosure.

Aspects of the present disclosure provide uses of the combinations an antibody of the present disclosure, in particular Antibody 1, and anti-N3pGlu Aβ antibodies, in particular donanemab, for methods of treating a disease characterized by deposition of Aβ in subjects, wherein the subjects are selected based on i) their tau level/burden in the whole brain (global tau), ii) their tau level/burden in regions of the brain (e.g., in different lobes of the brain), and/or the presence of one or two alleles of APOE e4 in the subject's genome. The diseases that can be treated or prevented using the combination methods disclosed herein include, e.g., Alzheimer's disease (AD), Down's syndrome, and cerebral amyloid angiopathy (CAA). The present disclosure is also related use of the combinations provided herein to slow disease progression in subjects with early symptomatic Alzheimer's disease (AD) in the presence of intermediate brain tau burden.

Antibodies to N3pGlu Aβ are known in the art and described herein. For example, U.S. Pat. No. 8,679,498 (which is hereby incorporated by reference in its entirety, including the anti-N3pGlu Aβ antibodies disclosed therein) discloses anti-N3pGlu Aβ antibodies and methods of treating diseases, such as, Alzheimer's disease, with the antibodies. Passive immunization by long term chronic administration of antibodies against Aβ, including N3pGlu Aβ, found in deposits has been shown to disrupt the Aβ aggregates and promote the clearance of plaques in the brain in various animal models. Donanemab (disclosed in U.S. Pat. No. 8,679,498, see also CAS number 1931944-80-7) is an antibody directed at the pyroglutamate modification of the third amino acid of amyloid beta (N3pGlu AD) epitope that is present only in brain amyloid plaques. The mechanism of action of donanemab is the targeting and removal of existing amyloid plaque, which is a key pathological hallmark of AD. A second neuropathological hallmark of AD is the presence of intracellular neurofibrillary tangles containing hyperphosphorylated tau protein. It is possible that Aβ triggers tau pathology, with a more complex and synergistic interaction between Aβ and tau manifesting at later stages and driving disease progression (Busche et al., "Synergy Between Amyloid-β and Tau in Alzheimer's disease,"*Nature Neuroscience* 23:1183-93 (2020)).

Administration of Aβ antibodies have led to adverse events in humans, such as, amyloid-related imaging abnormalities (ARIA), suggestive of vasogenic edema and sulcal effusions (ARIA-E), microhemorrhages and haemosiderin deposits (ARIA-H), infusion site reactions, and risk of immunogenicity. See, e.g., Piazza and Winblad, "Amyloid-Related Imaging Abnormalities (ARIA) in Immunotherapy Trials for Alzheimer's Disease: Need for Prognostic Biomarkers?" Journal of Alzheimer's Disease, 52:417-420 (2016); Sperling, et al., "Amyloid-related Imaging Abnormalities in Patients with Alzheimer's Disease Treated with Bapineuzumab: A Retrospective Analysis," The Lancet Neurology 11.3: 241-249 (2012); Brashear et al., "Clinical Evaluation of Amyloid-related Imaging Abnormalities in Bapineuzumab Phase III Studies," J. of Alzheimer's Disease 66.4:1409-1424 (2018); Budd et al., "Clinical Development of Aducanumab, an Anti-Aβ Human Monoclonal Antibody Being Investigated for the Treatment of Early Alzheimer's Disease," The Journal of Prevention of Alzheimer's Disease 4.4: 255 (2017).

A combination treatment strategy of the present disclosure for donanemab and Antibody 1 includes targeting N3pGlu Aβ specific to amyloid plaque in the population of early symptomatic AD patients with existing brain amyloid load and targeting neuroinflammation in these patients. This rationale is based on the amyloid hypothesis of AD, which states that the production and deposition of Aβ is an early and necessary event in the pathogenesis of AD. See, e.g., Selkoe, "The Origins of Alzheimer Disease: A is for Amyloid," *JAMA* 283:1615-1617 (2000). Clinical support for this hypothesis comes from the demonstration that parenchymal Aβ levels are elevated before the appearance of symptoms of AD and supported by genetic variants of AD that overproduce brain Aβ and genetic variants that protect against Aβ production. See, e.g., Jonsson et al., "A Mutation in APP Protects Against Alzheimer's Disease and Age-related Cognitive Decline," *Nature* 488 (7409):96-99 (2012) and Fleisher et al., "Associations Between Biomarkers and Age in the Presenilin 1 E280A Autosomal Dominant Alzheimer Disease Kindred: A Cross-sectional Study," *JAMA Neurol.* 72:316-24 (2015). Thus, a need exists for improved combinations of agents for treatment of subjects without causing or increasing problematic adverse events. Neuroinflammation is an important component of neurodegenerative diseases and is characterized by elevated production of pro-inflammatory cytokines by CNS cells. Neuroinflammation and microgliosis are believed to be mechanisms underlying Alzheimer's disease, and/or neuronal cell death and dysfunction. Microgliosis involves the abnormal proliferation and/or hypertrophy of microglia in response to inflammatory signals. IL-34 acts as a potent and pleiotropic cytokine in the regulation of inflammatory and immune processes, and is expressed by neurons in the cortex, the anterior olfactory nucleus and the hippocampus. Treatment with Antibody 1 simultaneously, separately, or preferably sequentially following treatment with N3pGlu Aβ antibodies, in particular donanemab, is conceived to ameliorate the contribution of neuroinflammation and/or microgliosis to AD pathogenesis and slow or prevent the progression of neurodegenerative processes in these patients.

One aspect of the present disclosure is based on the conception that Alzheimer's patients with low or moderate tau, very low to moderate tau, or not having high tau are responsive to combination treatment with anti-N3pGlu Aβ antibodies such as donanemab and antibodies of the present disclosure such as Antibody 1. Another aspect of the present disclosure is based on the conception that Alzheimer's patients having one or two alleles of APOE e4 are responsive to treatment with anti-N3pGlu Aβ antibodies. Yet another aspect of the present disclosure is based on the conception that Alzheimer's patients having one or two alleles of APOE e4 and low or moderate tau, very low to moderate tau, or not having high tau are responsive to combination treatment with anti-N3pGlu Aβ antibodies such as donanemab and antibodies of the present disclosure such as Antibody 1. Some aspects of the present disclosure are directed to diagnosing and treating patients based on their brain pathology. Selecting patients based on their brain pathology not only provides a more homogenous population in clinical trials but also ensures proper identification of the stage of AD and its progression. Proper identification of the stage of AD also allows, e.g., for a timely referral to a memory clinic, a correct and early AD diagnosis, initiation of symptomatic treatment, future planning, and initiating disease-modifying treatments with the combination treatment methods of anti-N3pGlu Aβ antibodies, such as donanemab, and antibodies of the present disclosure, such as Antibody 1.

Some aspects of the present disclosure provide for combination embodiments for treating a human subject, suffering from a disease characterized by Aβ deposits in their brain, wherein the subject is first administered an anti-N3pGlu Aβ antibody, such as donanemab, in two steps, combined with simultaneous, separate, or sequential treatment with an antibody of the present disclosure, such as Antibody 1. In a first step, the human subject is administered one or more first doses of about 100 mg to about 700 mg of the anti-N3pGlu Aβ antibody, wherein each first dose is administered once about every 4 weeks. About four weeks after administering the one or more first doses, the human subject is administered one or more second doses of greater than 700 mg to about 1400 mg in a second step, wherein each second dose is administered once every four weeks. Preferably the anti-N3pGlu Aβ antibody is donanemab. Antibody1 is administered simultaneously, separately, or sequentially following the course of treatment with donanemab. Preferably Antibody1 is administered sequentially following the course of treatment with donanemab.

Some aspects of the combination methods of treatment are related to identifying the stage/progression of AD in a patient based on i) the global or overall tau burden in the brain of a human subject or ii) the spread of tau in the subject's brain or regions or portions thereof.

In some embodiments, the patients can be stratified/identified/selected/treated based on the amount of tau present in the subject's brain (e.g., in the whole brain or in portions of the brain). In some embodiments, the patients can be stratified/identified/selected/treated based on the amount of tau present in the subject's brain (e.g., in the whole brain or in portions of the brain) and the presence of one or two alleles of APOE e4.

In other embodiments, the patients are stratified/identified/selected/treated based on stages of AD progression (e.g., based on the spread of tau in the brain). For example, during some stages, tau burden in an AD patient is isolated to frontal lobe or regions of the temporal lobe that do not include the posterolateral temporal region (PLT). Another stage of AD is where tau burden in an AD patient is limited to the posterolateral temporal (PLT) or occipital regions. Yet another stage of AD is when the tau burden in an AD patient is present in the parietal or precuneus region or in the frontal region along with tau burden in PLT or occipital regions. In some embodiments, the patients can be stratified/identified/selected/treated based on the stages of AD progression (e.g., based on the spread of tau in the brain) and the presence of one or two alleles of APOE e4.

The stratification of patients based on amount of tau in the brain, AD progression in portions of brain, and/or the presence of one or two alleles of APOE e4 can be used to determine, e.g., whether a patient will respond to combination treatments with anti-N3pGlu Aβ antibodies, such as donanemab, and antibodies of the present disclosure, such as Antibody 1. Stratification/selection of patient population based on amount of tau in the brain, AD progression in portions of brain, and/or the presence of one or two alleles of APOE e4 is also helpful in solving the patient heterogeneity and replicability problems faced during design and performance of clinical trials addition to treatment.

Other aspects of the present disclosure provide for human subjects that are responsive to the combination treatment or prevention with anti-N3pGlu Aβ antibodies, such as donanemab, and antibodies of the present disclosure, such as Antibody 1, for a disease characterized by amyloid beta (Aβ) deposits in the brain of a human subject. In some embodiments, of this aspect of the present disclosure, the responsive human subjects include human subjects having low to moderate tau burden, very low to moderate tau burden, and/or one or two alleles of APOE e4. In some embodiments, of this aspect of the present disclosure, the responsive human subjects exclude human subjects with high tau burden. In some embodiments, of this aspect of the present disclosure, the responsive human subjects exclude human subjects with high tau burden and/or with one or two alleles of APOE e4. In some embodiments, the combinations of anti-N3pGlu Aβ antibodies, such as donanemab, and antibodies of the present disclosure, such as Antibody 1, are administered to the responsive human subjects for treatment or prevention of a disease characterized by amyloid beta (Aβ) deposits in the brain of a human subject.

In one aspect, the present disclosure is related to the simultaneous, separate, or sequential combination treatment or prevention using anti-N3pGlu Aβ antibodies, in particular donanemab, and antibodies of the present disclosure, in particular Antibody 1, for a disease characterized by Aβ deposits in the brain of a human subject comprising: i) administering to the human subject one or more first doses of about 100 mg to about 700 mg of an anti-N3pGlu Aβ antibody, wherein each first dose is administered once about every 4 weeks and ii) about four weeks after administering the one or more first doses, administering to the human subject one or more second doses of greater than 700 mg to about 1400 mg of the anti-N3pGlu Aβ antibody, wherein each second dose is administered once about every 4 weeks, wherein the anti-N3pGlu Aβ antibody comprises donanemab, and administering to the human subject and Antibody of the present disclosure, in particular Antibody 1. Preferably Antibody1 is administered sequentially following a course of treatment with donanemab.

To date, clinical focus for treatment with donanemab has been specific to early symptomatic AD patients with existing brain amyloid load. However, a second neuropathological hallmark of AD is the presence of intracellular neurofibrillary tangles containing hyperphosphorylated tau protein. Current disease models suggest that Aβ triggers tau pathology, with a more complex and synergistic interaction between Aβ and tau manifesting at later stages and driving disease progression (Busche et al., "Synergy Between Amyloid-β and Tau in Alzheimer's disease," *Nature Neuroscience* 23:1183-93 (2020)).

There currently exists no disease-modifying treatment for AD. Thus, a need exists for improved methods of treating diseases, including Aβ, characterized by deposition of Aβ in a human subject. Such methods should aid in identifying patients based on whether such patient is likely to have a therapeutic benefit from such treatment. Such treatments and methods should further not be attendant upon increased cytotoxicity or other known adverse events. The present disclosure meets one of more of these needs.

Doody et al., "Phase 3 Trials of Solanezumab for Mild-to-Moderate Alzheimer's Disease,"*NEJM,* 370; 4, 311-321 (2014) indicate that "[n]o clear differential treatment effects on efficacy measures were observed between APOE F4 carriers and noncarriers." Administering an anti-N3pGlu Aβ antibody in combination with an antibody of the present disclosure to a human subject that has one or two alleles of APOE e4 (e.g., a carrier of APOE e4) is conceived to provide unexpected efficacy when compared to non-carriers of one or more of those alleles. Thus, the present embodiments include administering simultaneous, separate, or sequential doses of anti-N3pGlu Aβ antibodies, in particular donanemab, in combination with antibodies of the present disclosure, in particular Antibody 1, to patients who have one or two APOE e4 alleles as a means of slowing the cognitive decline of those patients.

According to particular embodiments, the present disclosure provides methods of treating or preventing a disease characterized by amyloid beta (Aβ) deposits in the brain of a human subject who has been determined to have a high neurological tau burden, comprising administering simultaneous, separate, or sequential doses of a therapeutically effective amount of an anti-AP antibody, and in particular donanemab, and a therapeutically effective amount of an antibody of the present disclosure, and in particular Antibody 1. Additionally, according to particular embodiments, the present disclosure provides combination methods of treating or preventing a disease characterized by Aβ deposits in the brain of a human subject who has been determined to have a posterior-lateral temporal lobe tau burden, comprising administering simultaneous, separate, or sequential doses of a therapeutically effective amount of an anti-AP antibody, and in particular donanemab, and a therapeutically effective amount of an antibody of the present disclosure, and in particular Antibody 1.

According to particular embodiments, the present disclosure provides combination methods of treating or preventing a disease characterized by amyloid beta (Aβ) deposits in the brain of a human subject who has been determined to have a high neurological tau burden and having one or two alleles of epsilon-4 allele of apolipoprotein E (referred to herein as APOE e4 or APOE4), comprising administering simultaneous, separate, or sequential doses of a therapeutically effective amount of an anti-AP antibody, and in particular donanemab, and a therapeutically effective amount of an antibody of the present disclosure, and in particular Antibody 1. Additionally, according to particular embodiments, the present disclosure provides methods of treating or preventing a disease characterized by Aβ deposits in the brain of a human subject who has been determined to have a posterior-lateral temporal lobe tau burden, comprising administering simultaneous, separate, or sequential doses of a therapeutically effective amount of an anti-AP antibody, and in particular donanemab, and a therapeutically effective amount of an antibody of the present disclosure, and in particular Antibody 1.

According to some embodiments, the present disclosure provides an anti-AP antibody, and in particular donanemab, for simultaneous, separate, or sequential use with an antibody of the present disclosure, and in particular Antibody 1, for the treatment or prevention of a disease characterized by Aβ deposits in the brain of a human subject who has been determined to have a high neurological tau burden, comprising administering simultaneous, separate, or sequential doses of a therapeutically effective amount of an anti-AP antibody, and in particular donanemab, and a therapeutically effective amount of an antibody of the present disclosure, and in particular Antibody 1. In some embodiments, the human subject has been determined to have a high neurological tau burden as well as having one or two alleles of APOE e4.

In some embodiments, the present disclosure provides an anti-AP antibody, and in particular donanemab, for simultaneous, separate, or sequential use with an antibody of the present disclosure, and in particular Antibody 1, for the treatment or prevention of a disease characterized by Aβ deposits in the brain of a human subject who has been determined to have a posterior-lateral temporal lobe tau burden. In some embodiments, the human subject has been determined to have a posterior-lateral temporal lobe tau burden as well as having one or two alleles of APOE e4.

Additionally, in some embodiments, the present disclosure provides an anti-AP antibody, and in particular donanemab, for simultaneous, separate, or sequential use with an antibody of the present disclosure, and in particular Antibody 1, for treating, preventing or retarding the progression of Alzheimer's Disease (AD). Additionally, in some embodiments, the present disclosure provides an anti-AP antibody, and in particular donanemab, for simultaneous, separate, or sequential use with an antibody of the present disclosure, and in particular Antibody 1, for treating, preventing or retarding the progression of Alzheimer's Disease (AD) in a human subject who has been determined to have slow progressing AD cognitive decline. Some embodiments of the present disclosure provide an anti-AP antibody, and in particular donanemab, for simultaneous, separate, or sequential use with an antibody of the present disclosure, and in particular Antibody 1, for treating, preventing or retarding the progression of Alzheimer's Disease (AD) in a human subject who has been determined to have slow progressing AD cognitive decline and one or two alleles of APOE e4.

Further, according to some embodiments, the present disclosure provides the use of an anti-AP antibody, in particular donanemab, in simultaneous, separate, or sequential combination with an antibody of the present disclosure, and in particular Antibody 1, in the manufacture of a medicament for treatment or prevention of Alzheimer's Disease. Further, according to some embodiments, the present disclosure provides the use of an anti-Aβ antibody, and in particular donanemab, in simultaneous, separate, or sequential combination with an antibody of the present disclosure, and in particular Antibody 1, in the manufacture of a medicament for treatment or prevention of a disease characterized by Aβ deposits in the brain of a human subject who has been determined to have a i) high neurological tau burden or ii) high neurological tau burden and one or two alleles of APOE e4.

In some embodiments, the present disclosure provides for the use of an anti-Aβ antibody, in particular donanemab, in simultaneous, separate, or sequential combination with an antibody of the present disclosure, and in particular Antibody 1, in the manufacture of a medicament for treatment or prevention of a disease characterized by Aβ deposits in the brain of a human subject who has been determined to have i) a posterior-lateral temporal lobe tau burden or ii) a posterior-lateral temporal lobe tau burden and one or two alleles of APOE e4. And in further embodiments, the present disclosure provides for the use of an anti-Aβ antibody, in particular donanemab, in simultaneous, separate, or sequential combination with an antibody of the present disclosure, and in particular Antibody 1, in the manufacture of a medicament for treating, preventing or retarding the progression of Alzheimer's Disease (AD) in a human subject who has been determined to have i) slow progressing AD cognitive decline or ii) one or two alleles of APOE e4 and slow progressing AD cognitive decline.

According to some of the embodiments provided herein, the human subject has been determined to have posterior-lateral temporal lobe and occipital lobe tau burden. In some embodiments, the human subject has been determined to have posterior-lateral temporal lobe, occipital lobe and parietal lobe tau burden. In some embodiments, the human subject has been determined to have posterior-lateral temporal lobe, occipital lobe, parietal lobe and frontal lobe tau burden. In some embodiments, the human subject has been determined to have one or more of posterior-lateral temporal lobe, occipital lobe, parietal lobe and/or frontal lobe tau burden by neurological PET imaging. In some embodiments, the one or more of posterior-lateral temporal lobe, occipital lobe, parietal lobe and/or frontal lobe tau burden corresponds a neurological tau burden of greater than 1.46 SUVr.

According to some of the embodiments provided herein, the human subject has been determined to have one or two alleles of APOE e4 and posterior-lateral temporal lobe and occipital lobe tau burden. In some embodiments, the human subject has been determined to have one or two alleles of APOE e4 and posterior-lateral temporal lobe, occipital lobe and parietal lobe tau burden. In some embodiments, the human subject has been determined to have one or two alleles of APOE e4 and posterior-lateral temporal lobe, occipital lobe, parietal lobe and frontal lobe tau burden. In some embodiments, the human subject has been determined to have one or more of posterior-lateral temporal lobe, occipital lobe, parietal lobe and/or frontal lobe tau burden by neurological PET imaging and one or two alleles of APOE e4. In some embodiments, the one or more of posterior-lateral temporal lobe, occipital lobe, parietal lobe and/or frontal lobe tau burden corresponds a neurological tau burden of greater than 1.46 SUVr.

According to additional embodiments, the present disclosure provides methods of treating, preventing, or retarding the progression of Alzheimer's Disease (AD) in a human subject who has been determined to have slow progressing AD cognitive decline, comprising administering simultaneous, separate, or sequential doses of a therapeutically effective amount of an anti-Aβ antibody, and in particular donanemab, and a therapeutically effective amount of an antibody of the present disclosure, and in particular Antibody 1. According to some embodiments, the human subject has been determined to have a high neurological tau burden. According to some embodiments, the human subject has been determined to have one or two alleles of APOE e4. In some embodiments, the human subject has been determined to have posterior-lateral temporal lobe tau burden. In some embodiments, the human subject has been determined to have posterior-lateral temporal lobe and occipital lobe tau burden. In some embodiments, the human subject has been determined to have posterior-lateral temporal lobe, occipital lobe and parietal lobe tau burden. In some embodiments, the human subject has been determined to have posterior-lateral temporal lobe, occipital lobe, parietal lobe and frontal lobe tau burden. In some embodiments, the human subject has been determined to have posterior-lateral temporal lobe tau burden and one or two alleles of APOE e4. In some embodiments, the human subject has been determined to have one or two alleles of APOE e4 and posterior-lateral temporal lobe and occipital lobe tau burden. In some embodiments, the human subject has been determined to have one or two alleles of APOE e4 and posterior-lateral temporal lobe, occipital lobe and parietal lobe tau burden. In some embodiments, the human subject has been determined to have one or two alleles of APOE e4 and posterior-lateral temporal lobe, occipital lobe, parietal lobe and frontal lobe tau burden.

According to embodiments of the present disclosure provided herein, the human subject has been determined to have slow progressing AD cognitive decline by one of more of ADAS-Cog, iADL, CDR-SB, MMSE, APOE-4 genotyping and/or iADRS. In some embodiments, the human subject has been determined to have slow progressing AD cognitive decline by iADRS. In some embodiments, iADRS has declined by less than 20. In some embodiments, iADRS has declined by less than 20 over a 6 month period. In some embodiments, iADRS has declined by less than 20 over a 12 month period. In some embodiments, iADRS has declined by less than 20 over an 18 month period. In some embodiments, iADRS has declined by less than 20 over a 24 month period. In some embodiments, the human subject has been determined to have slow progressing AD cognitive decline by APOE-4 genotyping. In some embodiments, the human subject has been determined to be APOE-4 heterozygous. In some embodiments, the human subject has been determined to be APOE-4 homozygous negative. In some embodiments, the human subject has been determined to have slow progressing AD cognitive decline by MMSE. In some embodiments, the human subject has been determined to have MMSE of above 27. In some embodiments, MMSE has declined by less than 3. In some embodiments, MMSE has declined by less than 3 over a 6 month period. In some embodiments, MMSE has declined by less than 3 over a 12 month period. In some embodiments, MMSE has declined by less than 3 over a 18 month period. In some embodiments, MMSE has declined by less than 3 over a 24 month period.

According to embodiments of the present disclosure provided herein, the human subject has been determined to have a high neurological tau burden by neurological PET imaging. In some embodiments, the human subject has been determined to have high neurological tau burden by neurological PET imaging above 1.46 SUVr. In some embodiments, the human subject has been determined to have high neurological tau burden by quantification of human tau phosphorylated at threonine at residue 217 ("hTau-pT217"). In some embodiments, hTau-pT217 is quantified in a biological sample of the human subject. In some embodiments, the biological sample is cerebral spinal fluid. In some embodiments, the biological sample is one of blood, plasma or serum.

For the purposes of the present invention, the tau level or burden (as used interchangeably herein) of a human subject can be determined using techniques or methods that, e.g., detect or quantitate i) neurological or brain tau deposition, ii) tau in blood, serum and/or plasma, or iii) tau in cerebrospinal fluid. In some embodiments, neurological tau burden (whether determined via PET or via a blood, serum, plasma or cerebrospinal fluid assay) can be used to stratify subjects based on neurological tau burden (e.g., low, moderate or high neurological tau burden).

Neurological tau burden can be determined using methods, such as, tau imaging with radiolabeled PET compounds (Leuzy et al., "Diagnostic Performance of R0948 F18 Tau Positron Emission Tomography in the Differentiation of Alzheimer Disease from Other Neurodegenerative Disorders,"*JAMA Neurology* 77.8:955-965 (2020); Ossenkoppele et al., "Discriminative Accuracy of [$^{18}$F]-flortaucipir Positron Emission Tomography for Alzheimer Disease vs Other Neurodegenerative Disorders," *JAMA* 320, 1151-1162, doi: 10.1001/jama.2018.12917 (2018), which are hereby incorporated by reference in their entireties) including [$^{18}$F]-florbtaucipir, which is a PET ligand. PET tau images can be, for example, quantitatively evaluated to estimate an SUVr (standardized uptake value ratio) by published methods (Pontecorvo et al., "A Multicentre Longitudinal Study of Flortaucipir (18F) in Normal Ageing, Mild Cognitive Impairment and Alzheimer's Disease Dementia," *Brain* 142: 1723-35 (2019); Devous et al., "Test-Retest Reproducibility for the Tau PET Imaging Agent Flortaucipir F18," *Journal of Nuclear Medicine* 59:937-43 (2018); Southekal et al., "Flortaucipir F18 Quantitation Using Parametric Estimation of Reference Signal Intensity," *J. Nucl. Med.* 59:944-51 (2018), which are hereby incorporated by reference in their entireties) and/or to visually evaluate patients, e.g., to determine whether the patient has an AD pattern (Fleisher et al., "Positron Emission Tomography Imaging With [$^{18}$F]-flortaucipir and Postmortem Assessment of Alzheimer Disease Neuropathologic Changes,"*JAMA Neurology* 77:829-39 (2020), which is hereby incorporated by reference in its entirety). Lower SUVr values indicate less tau burden while higher SUVr values indicate a higher tau burden. In an embodiment, quantitative assessment by a flortaucipir scan is accomplished through an automated image processing pipeline as described in Southekal et al., "Flortaucipir F18 Quantitation Using Parametric Estimation of Reference Signal Intensity," *J. Nucl. Med* 59:944-951 (2018), which is hereby incorporated by reference in its entirety. In some embodiments, counts within a specific target region of interest in the brain (e.g., multiblock barycentric discriminant analysis or MUBADA, see Devous et al, "Test-Retest Reproducibility for the Tau PET Imaging Agent Flortaucipir F18," *J. Nucl. Med.* 59:937-943 (2018), which is hereby incorporated by reference in its entirety) are compared with a reference region wherein the reference region is, e.g., whole cerebellum, (wholeCere), cerebellar GM (cereCrus), atlas-based white matter (atlasWM), subject-specific WM (ssWM, e.g., using parametric estimate of reference signal intensity (PERSI), see Southekal et al., "Flortaucipir F18 Quantitation Using Parametric Estimation of Reference Signal Intensity," *J. Nucl. Med* 59:944-951 (2018), which is hereby incorporated by reference in its entirety). An exemplary method of determining tau burden is a quantitative analysis reported as a standardized uptake value ratio (SUVr), which represents counts within a specific target region of interest in the brain (e.g., MUBADA) when compared with a reference region (e.g., using PERSI).

In some embodiments, phosphorylated tau (P-tau; either phosphorylated at threonine 181 or 217, or a combination thereof) can be used to measure the tau load/burden for the purposes of the present disclosure (Barthelemy et al., "Cerebrospinal Fluid Phospho-tau T217 Outperforms T181 as a Biomarker for the Differential Diagnosis of Alzheimer's Disease and PET Amyloid-positive Patient Identification, "*Alzheimer's Res. Ther.* 12, 26, doi:10.1186/s13195-020-00596-4 (2020); Mattsson et al., "Aβ Deposition is Associated with Increases in Soluble and Phosphorylated Tau that Precede a Positive Tau PET in Alzheimer's Disease,"*Science Advances* 6, eaaz2387 (2020), which are hereby incorporated by reference their entireties). In a particular embodiment, antibodies directed against human tau phosphorylated at threonine at residue 217 can be used to measure the tau load/burden in a subject (see International Patent Application Publication No. WO 2020/242963, which is incorporated by reference in its entirety). The present disclosure includes, in some embodiments, the use of anti-tau antibodies disclosed in WO 2020/242963 to measure the tau load/burden in a subject. Anti-tau antibodies disclosed in WO 2020/242963 are directed against isoforms of human tau expressed in the CNS (e.g., recognizing the isoforms expressed in the CNS and not recognizing isoforms of human tau expressed exclusively outside the CNS).

A subject is positive for amyloid deposits when amyloid is detected in the brain by methods such as, amyloid imaging with radiolabeled PET compounds or using a diagnostic that detects Aβ or a biomarker for Aβ. Exemplary methods that can be used to measure the brain amyloid load/burden include, e.g., Florbetapir (Carpenter, et al., "The Use of the Exploratory IND in the Evaluation and Development of $^{18}$F-PET Radiopharmaceuticals for Amyloid Imaging in the Brain: A Review of One Company's Experience,"*The Quarterly Journal of Nuclear Medicine and Molecular Imaging* 53.4:387 (2009), which is hereby incorporated by reference in its entirety); Florbetaben (Syed et al., "[$^{18}$F]Florbetaben: A Review in β-Amyloid PET Imaging in Cognitive Impairment," *CNSDrugs* 29, 605-613 (2015), which is hereby incorporated by reference in its entirety); and Flutemetamol (Heurling et al., "Imaging 0-amyloid Using [$^{18}$F] Flutemetamol Positron Emission Tomography: From Dosimetry to Clinical Diagnosis," *European Journal of Nuclear Medicine and Molecular Imaging* 43.2: 362-373 (2016), which is hereby incorporated by reference in its entirety). [$^{18}$F]-florbetapir can provide a qualitative and quantitative measurement of brain plaque load in patients, including patients with prodromal AD or mild AD dementia and can be used to assess amyloid plaque reductions from the brain as well.

Additionally, cerebrospinal fluid or plasma-based analysis of 0-amyloid can also be used to measure the amyloid load/burden. For example, A042 can be used to measure brain amyloid (Palmqvist, S. et al., "Accuracy of Brain Amyloid Detection in Clinical Practice Using Cerebrospinal Fluid Beta-amyloid 42: a Cross-validation Study Against Amyloid Positron Emission Tomography. *JAMA Neurol* 71, 1282-1289 (2014), which is hereby incorporated by reference in its entirety). In some embodiments, the ratio of Aβ42/Aβ40 or Aβ42/Aβ38 can be used as a biomarker for amyloid beta (Janelidze et al., "CSF Abeta42/Abeta40 and Abeta42/Abeta38 Ratios: Better Diagnostic Markers of Alzheimer Disease," *Ann Clin Transl Neurol* 3, 154-165 (2016), which is hereby incorporated by reference in its entirety). In some embodiments, deposited brain amyloid plaque or Aβ in CSF or plasma can be used to stratify subjects into groups based on amyloid load/burden.

Use of Antibody 1 for the Treatment or Prevention of ARIA:

In some embodiments, the present disclosure provides the use of Antibody 1 for the treatment or prevention of ARIA. Several therapeutic amyloid targeted antibodies have demonstrated dose-response related increases in ARIA-E. See, e.g., Brashear et al., "Clinical Evaluation of Amyloid-related Imaging Abnormalities in Bapineuzumab Phase III Studies," *J. of Alzheimer's Disease* 66.4:1409-1424 (2018); Budd et al., "Clinical Development of Aducanumab, an Anti-Aβ Human Monoclonal Antibody Being Investigated for the Treatment of Early Alzheimer's Disease," *The Journal of Prevention of Alzheimer's Disease* 4.4: 255 (2017). ARIA-E and ARIA-H have been associated with amyloid plaque-removing treatments (Sperling et al., "Amyloid-related imaging abnormalities in amyloid-modifying therapeutic trials: Recommendations from the Alzheimer's Association Research Roundtable Workgroup," *Alzheimer's & Dementia* 7:367-85 (2011); Sevigny et al., "The Antibody Aducanumab Reduces Aβ Plaques in Alzheimer's Disease," *Nature* 537:50-6 (2016); Ostrowitzki et al., "Mechanism of Amyloid Removal in Patients With Alzheimer Disease Treated With Gantenerumab," *Archives of Neurology* 69:198-207 (2012); Salloway et al., "Two Phase 3 Trials of Bapineuzumab in Mild-to-Moderate Alzheimer's Disease," *New England Journal of Medicine* 370:322-33 (2014); Salloway et al., "A Phase 2 Multiple Ascending Dose Trial of Bapineuzumab in Mild to Moderate Alzheimer Disease," Neurology 73:2061-70 (2009); and Sperling et al., "Amyloid-related Imaging Abnormalities in Patients with Alzheimer's Disease Treated with Bapineuzumab: A Retrospective Analysis," *Lancet Neurol.* 11:241-9 (2012), which are hereby incorporated by reference in their entireties).

As used herein "amyloid-related imaging abnormalities" and "ARIA" are interchangeable and include vasogenic edema and sulcal effusions (ARIA-E) and microhemorrhages and haemosiderin deposits (ARIA-H), and represent underlying pathological conditions recognized by the skilled artisan (See e.g., Amyloid-Related Imaging Abnormalities and β-Amyloid-Targeting Antibodies, A Systematic Review, Massimo Filippi, M D; et al., JAMA Neurol. 2022; 79(3): 291-304, and Amyloid-Related Imaging Abnormalities with Emerging Alzheimer Disease Therapeutics: Detection and Reporting Recommendations for Clinical Practice, P. M. Cogswell, et al., Am J Neuroradiol 43:E19-E35 September 2022). ARIA can be scored on a scale from 0-5. Although the exact cause of such adverse events is not known, it is generally believed that anti-amyloid antibody treatment disrupts blood-brain barrier through interaction with the cerebral vascular amyloid and that this disruption leads to leaky barrier and the manifestation of edema in patients. Several possible mechanisms of action have been postulated, e.g., that removal of amyloid from the vessel wall destabilizes the neurovascular unit, localized inflammation/infiltrates in the neurovascular unit, increased levels of cerebral vascular amyloid due to higher levels of interstitial soluble Aβ in response to parenchymal plaque clearance or altered localization of AQP-4 in astrocytic end feet projections in the neurovascular unit.

Amyloid deposition in vessel walls (CAA) may result in loss of vascular integrity and reduced perivascular clearance and may be related to spontaneously occurring microhemorrhages. When anti-amyloid monoclonal antibody therapy is initiated, antibody-mediated breakdown of amyloid plaque and mobilization of parenchymal and vascular Aβ increase the load of perivascular drainage. The overload of perivascular drainage pathways may transiently increase amyloid deposition in the arterial wall. At the same time, antibody-mediated inflammation and breakdown of amyloid also occur in the vessel wall. These processes cause further loss of vascular integrity and blood-brain barrier breakdown. As a result, proteinaceous fluid and/or red blood cells leak into the parenchyma and/or leptomeningeal space and result in edema/effusion (ARIA-E) or microhemorrhages/superficial siderosis (ARIA-H).

Methods of identifying a patient in need of treatment or prevention of ARIA are known to the skilled artisan, for instance as described in Amyloid-Related Imaging Abnormalities with Emerging Alzheimer Disease Therapeutics: Detection and Reporting Recommendations for Clinical Practice, P. M. Cogswell, et al., Am J Neuroradiol 43:E19-E35 September 2022, Detection and Management of Amyloid-Related Imaging Abnormalities in Patients with Alzheimer's Disease Treated with Anti-Amyloid Beta Therapy, J. Barakos et al., J Prev Alz Dis 2022; 2(9):211-220 (incorporated herein by reference), and other preceding references herein.

ARIA-E is most frequently detected on routine, protocol-specified, surveillance MRIs in patients who are clinically asymptomatic. When ARIA-E is symptomatic, the symptoms are most commonly non-localizing, such as headache or confusion, but can additionally include visual disturbances, visuospatial impairment, or praxis difficulties in view of the relative predilection for posterior involvement of ARIA-E. The E in ARIA-E stands for edema, effusion, and exudate. A leak of proteinaceous fluid into the parenchyma results in edema, with the imaging appearance similar to that of vasogenic edema and best visualized on a T2-FLAIR sequence. T2-hyperintense signal occurs in the white matter, gray matter, or both. There may be associated local mass effect and gyral swelling. Findings may be differentiated from cytotoxic edema by absent diffusion restriction; intense diffusion restriction associated with an acute infarct is not a characteristic of ARIA. When the leak occurs in the leptomeningeal space, the result is a sulcal effusion or exudate, only appreciated on T2-FLAIR sequences due to T1-shortening related to proteinaceous content. ARIA-E may present as either parenchymal edema or sulcal effusion, or both may occur together; sulcal effusion was the most common manifestation of ARIA-E in some antibody trial analyses, and parenchymal edema, in others. ARIA-E most commonly affects the occipital lobes followed by the parietal, frontal, and temporal lobes and, least frequently, the cerebellum. The intensity and size of the signal abnormality are variable, from subtle small, 1- to 2-cm zones of cortico-subcortical abnormality to multifocal-to-near hemispheric signal T2-hyperintense signal alterations. These regions of signal abnormality generally have ill-defined margins, though they may infrequently have circumscribed margins and mimic a neoplastic lesion. (See e.g., Amyloid-Related Imaging Abnormalities with Emerging Alzheimer Disease Therapeutics: Detection and Reporting Recommendations for Clinical Practice, P. M. Cogswell, et al., Am J Neuroradiol 43:E19-E35 September 2022).

ARIA-H, hemorrhage, includes microhemorrhages and superficial siderosis. When a leakage of heme products occurs in the parenchyma, microhemorrhages develop. Microhemorrhages are punctate, rounded, and markedly hypointense foci in the brain parenchyma on T2 sequences, measuring <10 mm in diameter. A leak of heme products into the leptomeningeal or subpial space results in superficial siderosis, which manifests as curvilinear hypointensity along the brain surface. Lobar macrohemorrhage (focus of hemorrhage identifiable on T1- or T2-weighted imaging, and usually >10 mm in diameter on gradient recalled-echo [GRE]) rarely occurs with anti-amyloid agents, and when it does, it may be the result of an underlying disease process such as CAA. (See eg. Amyloid-Related Imaging Abnormalities with Emerging Alzheimer Disease Therapeutics: Detection and Reporting Recommendations for Clinical Practice, P. M. Cogswell, et al., Am J Neuroradiol 43:E19-E35 September 2022).

In some instances, there is a higher incidence rate of ARIA-E in patients harboring the epsilon-4 allele of apolipoprotein E (referred to herein as APOE e4 or APOE4). Subjects having one or more copies of APOE4 are at higher risk and likely higher need for prevention and or therapy. Monitoring for need of prevention or treatment could include genotyping, family history, as well as MRI or CT imaging as described above, and monitoring known symptoms consistent with ARIA. Patients with amyloid disease of the blood vessels or brain parenchyma may be at risk of ARIA and are subject in need of Antibody 1 for prevention or treatment of ARIA.

Thus, a need exists for improved methods to treat or prevent ARIA in patients, such as AD patients, being treated with therapeutic amyloid targeted antibodies. In particular there is a need for simultaneous, separate, or sequential combinations of an antibody of the present disclosure, in particular Antibody 1, and one or more therapeutic amyloid targeted antibodies, wherein Antibody 1, is used to prevent or treat ARIA. Some known anti-AB antibodies for which amyloid targeted treatment may result in ARIA include donanemab, bapineuzumab, gantenerumab, aducanumab, GSK933776, solanezumab, crenezumab, ponezumab, and lecanemab (BAN2401), or an anti-N3pGlu Aβ antibody.

The present disclosure further provides simultaneous, separate, or sequential combinations of Antibody 1 and one or more therapeutic amyloid targeted antibodies, to prevent or treat ARIA. In some embodiments the therapeutic amyloid targeted antibodies for which treatment may be associated with ARIA include donanemab, bapineuzumab, gantenerumab, aducanumab, GSK933776, solanezumab, crenezumab, ponezumab, and lecanemab (BAN2401), or an anti-N3pGlu Aβ antibody.

In these embodiments an "anti-N3pGlu Aβ antibody," "anti-N3pG antibody," or "anti-N3pE antibody" can be used interchangeably and refer to an antibody that binds preferentially to N3pGlu Aβ over Aβ1-40 or Aβ1-42. One of ordinary skill in the art will appreciate and recognize that "anti-N3pGlu Aβ antibody", and several specific antibodies, including, "hE8L", "B12L" and "R17L" are identified and disclosed (along with methods for making and using such antibodies) in U.S. Pat. No. 8,679,498 B2 (which is hereby incorporated by reference in its entirety). See, for example, Table 1 of U.S. Pat. No. 8,679,498 B2. Each of the antibodies disclosed in U.S. Pat. No. 8,679,498 B2, including "hE8L", "B12L" and "R17L" antibodies, may be used as the anti-N3pGlu Aβ antibody of the present disclosure or in place of the anti-N3pGlu Aβ antibodies described in various aspects of the present invention. An anti-N3pGlu Aβ antibody of the present combination methods is the antibody comprising the HC and LC of SEQ ID NO's: 40 and 41, respectively. Other representative species of an anti-N3pGlu Aβ antibody include, but are not limited to, antibodies disclosed U.S. Pat. Nos. 8,961,972; 10,647,759; 9,944,696; WO 2010/009987A2; WO 2011/151076A2; WO 2012/136552A1 and equivalents thereto, e.g., under 35 U.S.C 112(f). One aspect of the present disclosure provides the use of Antibody 1 for the prevention or treatment of ARIA that have been observed in patients receiving anti-N3pGlu Aβ antibody.

One aspect of the present disclosure provides the use of Antibody 1 for the prevention or treatment of ARIA that have been observed in patients receiving therapeutic antibodies that bind to deposited amyloid and has been dose limiting for some clinical development programs.

In an embodiment, the present disclosure provides a method of preventing ARIA comprising administering to a patient in need thereof an effective amount of an anti-IL-34 antibody of the present disclosure. In an embodiment, the present disclosure provides a method of preventing ARIA comprising administering to a patient in need thereof an effective amount of Antibody 1. In an embodiment, the present disclosure provides a method of treating ARIA comprising administering to a patient in need thereof an effective amount of an anti-IL-34 antibody of the present disclosure. In an embodiment, the present disclosure provides a method of treating ARIA comprising administering to a patient in need thereof an effective amount of Antibody 1.

The present disclosure also provides an anti-IL-34 antibody of the present disclosure for use in prevention or treatment of ARIA. The present disclosure also provides Antibody 1 for use in prevention or treatment of ARIA.

In certain embodiments, the present disclosure provides the use of an anti-IL-34 antibody of the present disclosure in the manufacture of a medicament for the prevention or treatment of ARIA.

Additional embodiments of the combination uses and methods of using an antibody of the present disclosure are provided below. The combination embodiments may refer to Antibody 1, however embodiments further comprise the analogous methods, uses, and all limitations described herein for Antibodies of the present disclosure as described herein. The combination embodiments may refer to "an anti-N3pG Aβ antibody", which refers to each of the anti-N3pG Aβ antibodies described herein, however for clarity these embodiments further comprise the analogous methods, uses, and all limitations described herein for each of the anti-N3pG Aβ antibodies individually, and for example, preferably to combination uses of donanemab. Below are provided additional embodiments of the present disclosure which are numbered and include internal references to other numbered embodiments. For clarity these embodiments are to be read together with the numbered embodiments to which they refer, individually and/or collectively. The embodiments described below begin at number 26. The term "course of treatment" refers to the specific patient or subject, antibodies recited, doses recited, frequencies and or durations cited, order recited, and any other limitations, to the extent described in each instance.

Further combination embodiments of the present disclosure include:

26. A method of treating or preventing a disease characterized by amyloid beta (Aβ) deposits in the brain of a human subject comprising administering to the human subject in need thereof an effective amount of an anti-N3pG Aβ antibody in simultaneous, separate, or sequential combination with an effective amount of Antibody 1.

27. The method of embodiment 26 wherein the anti-N3pG Aβ antibody is donanemab.

28. The method of embodiment 26 where the disease is Alzheimer's disease.

29. The method of embodiment 26 wherein the anti-N3pG Aβ antibody is donanemab and the disease is Alzheimer's disease.

30. The method of embodiment 29 wherein Antibody 1 is administered sequentially after a course of treatment with donanemab.

31. A method of treating or preventing a disease characterized by amyloid beta (Aβ) deposits in the brain of a human subject comprising:
i) administering to the human subject one or more first doses of about 100 mg to about 700 mg of an anti-N3pG Aβ antibody, wherein each first dose is administered once about every four weeks; and
ii) about four weeks after administering the one or more first doses, administering to the human subject one or more second doses of greater than 700 mg to about 1400 mg of the anti-N3pG Aβ antibody, wherein each second dose is administered once about every 4 weeks, wherein the anti-N3pGlu Aβ antibody is donanemab, and
iii) simultaneously, separately, or sequentially administering to the human subject an effective amount of Antibody 1.

32. The method of embodiment 31, wherein the human subject is administered the first dose of donanemab once, two times, or three times before administering the second dose.

33. The method of embodiments 31 or 32, wherein the human subject is administered first doses of donanemab of about 700 mg.

34. The method of any one of embodiments 31 to 33, wherein the human subject is administered one or more second doses of donanemab of about 800 mg, about 900 mg, about 1000 mg, about 1100 mg, about 1200 mg, about 1300 mg, or about 1400 mg.

35. The method of any one of embodiments 31 to 34, wherein the human subject is administered one or more second doses of donanemab of about 1400 mg.

36. The method of any one of embodiments 31 to 35, wherein the anti-N3pGlu Aβ antibody is administered to the human subject for a course of treatment duration of up to 72 weeks or until normal level of amyloid is achieved.

37. The method of any one of embodiments 31 to 36, wherein the anti-N3pGlu Aβ antibody is administered to the human subject until the amyloid plaque level in the patient is about 25 centiloids or lower.

38. The method of any one of embodiments 31 to 36, wherein the anti-N3pGlu Aβ antibody is administered for a course of treatment to the human subject until the amyloid plaque level in the human subject is about 25 centiloids or lower for two consecutive PET imaging scans, optionally, wherein the two consecutive PET 39. The method of any one of embodiments 31 to 36, wherein the human subject is administered three first doses of donanemab of 700 mg once every four weeks and then second doses of 1400 mg once every four weeks for a course of treatment duration of up to 72 weeks.
40. The method of any one of embodiments 31 to 36, wherein the human subject is administered three first doses of 700 mg once every four weeks and then second doses of 1400 mg once every four weeks until the amyloid plaque level in the subject is about 25 centiloids or lower.
41. The method of any one of embodiments 31 to 36, wherein the human subject is administered three first doses of donanemab of 700 mg once every four weeks and then second doses of 1400 mg once every four weeks until amyloid plaque level in the subject is about 25 centiloids or lower for two consecutive PET imaging scans, optionally, wherein the two consecutive PET imaging scans are at least 6 months apart, or about 11 centiloids or lower for one PET imaging scan.
42. The method of any one of embodiments 31 to 41, wherein the human subject is administered the second dose of donanemab for a course of treatment duration sufficient to treat or prevent the disease.
43. The method of any one of embodiments 31 to 42, wherein the treatment or prevention of the disease causes i) reduction in Aβ deposits in the brain of the human subject and/or ii) slows cognitive or functional decline in the human subject.
44. The method of embodiment 43, wherein the reduction in Aβ deposits in the brain of the human subject is determined by amyloid PET brain imaging or a diagnostic that detects a biomarker for Aβ.
45. The method of embodiments 43 or 44, wherein the second dose is administered to the human subject until there is about 20-100% reduction in Aβ deposits in the brain of the human subject.
46. The method of embodiment 45, wherein the Aβ deposits in the brain of the human subject are reduced by about 20%, about 25%, about 30%, about 35%, about 40%, about 45%, about 50%, about 75% or about 100%.
47. The method of any one of embodiments 31 to 44, wherein the second dose of donanemab is administered to the human subject until the Aβ deposits in the brain of the human subject are reduced by i) about an average of about 25 centiloids to about 100 centiloids, ii) about an average of about 50 centiloids to about 100 centiloids, iii) about 100 centiloids, or iv) about 84 centiloids.
48. The method of any one of the embodiments 31 to 47, wherein the disease characterized by Aβ deposit in the brain of the human subject is selected from preclinical Alzheimer's disease (AD), clinical Aβ, prodromal Aβ, mild Aβ, moderate Aβ, severe AD, Down's syndrome, clinical cerebral amyloid angiopathy, or pre-clinical cerebral amyloid angiopathy.
49. The method of any one of embodiments 31 to 48, wherein the human subject is an early symptomatic AD patient.
50. The method of embodiment 49, wherein the human subject has prodromal AD and mild dementia due to AD.
51. The method of anyone of embodiments 26-50, wherein the human subject has: i) very low to moderate tau burden or has been determined to have very low to moderate tau burden, ii) low to moderate tau burden or has been determined to have low to moderate tau burden, iii) very low to moderate tau burden or has been determined to have very low to moderate tau burden and one or two alleles of APOE e4, iv) low to moderate tau burden or has been determined to have low to moderate tau burden and one or two alleles of APOE e4, or v) one or two alleles of APOE e4.
52. The method of embodiment 51, wherein the human subject has i) very low to moderate tau burden if the tau burden as measured by PET brain imaging is ≤1.46 SUVr or ii) low to moderate tau burden if the tau burden as measured by PET brain imaging is from 1.10 SUVr to 1.46 SUVr.
53. The method of anyone of embodiments 26-50, wherein the human subject i) does not have high tau burden or has been determined to not have a high tau burden or ii) carries one or two alleles of APOE e4 and does not have high tau burden or has been determined to not have a high tau burden.
54. The method of embodiments 53, wherein the human subject has high tau burden if the tau burden as measured by PET brain imaging is above 1.46 SUVr.
55. The method of embodiments 51 or 53, wherein the tau burden of the human subject is determined using PET brain imaging or a diagnostic that detects a biomarker for tau.
56. Use of an anti-N3pGlu Aβ antibody in simultaneous, separate, or sequential combination with Antibody 1 in the manufacture of a medicament for treatment or prevention of a disease characterized by Aβ deposits in the brain of a human subject, wherein one or more first doses of about 100 mg to about 700 mg of the anti-N3pGlu Aβ antibody are administered, wherein each first dose is administered once about every 4 weeks followed by administration of one or more second doses of greater than 700 mg to about 1400 mg four weeks after administering the one or more first doses, wherein each second dose of anti-N3pGlu Aβ antibody is administered once about every 4 weeks, and wherein the anti-N3pGlu Aβ antibody is donanemab.
57. The use of embodiment 56, wherein the human subject is administered the first dose of donanemab once, two times, or three times before administering the second doses of donanemab.
58. The use of embodiments 56 or 57, wherein the human subject is administered three first doses of donanemab of about 700 mg.
59. The use of any one of embodiments 56-58, wherein the human subject is administered one or more second doses of donanemab of about 800 mg, about 900 mg, about 1000 mg, about 1100 mg, about 1200 mg, about 1300 mg, or about 1400 mg.
60. The use of any one of embodiments 56-59, wherein the human subject is administered one or more second doses of donanemab of about 1400 mg.
61. The use of any one of embodiments 56-60, wherein the anti-N3pGlu Aβ antibody is administered to the human subject for a course of treatment duration of up to 72 weeks or until normal level of amyloid is achieved.
62. The use of any one of embodiments 56-61, wherein the anti-N3pGlu Aβ antibody is administered to the 63. The use of any one of embodiments 56-61, wherein the anti-N3pGlu Aβ antibody is administered to the human subject until the amyloid plaque level in the patient is about 25 centiloids or lower for two consecutive PET imaging scans, optionally, wherein the two consecutive PET imaging scans are at least 6 months apart, or about 11 centiloids or lower for one PET imaging scan.

64. The use of any one of embodiments 56-61, wherein the human subject is administered three first doses of donanemab of 700 mg once every four weeks and then second doses of donanemab of 1400 mg once every four weeks for a duration of up to 72 weeks.

65. The use of any one of embodiments 56-61, wherein the human subject is administered three first doses of donanemab of 700 mg once every four weeks and then second doses of donanemab of 1400 mg once every four weeks until the amyloid plaque level in the patient is about 25 centiloids or lower.

66. The use of any one of embodiments 56-61, wherein the human subject is administered three first doses of donanemab of 700 mg once every four weeks and then second doses of donanemab of 1400 mg once every four weeks until amyloid plaque level in the patient is about 25 centiloids or lower for two consecutive PET imaging scans, optionally, wherein the two consecutive PET imaging scans are at least 6 months apart, or about 11 centiloids or lower for one PET imaging scan.

67. The use of any one of embodiments 56-66, wherein the human subject is administered the second dose of donanemab for a course of treatment duration sufficient to treat or prevent the disease.

68. The use of any one of embodiments 56-67, wherein the treatment or prevention of the disease causes i) reduction in Aβ deposits in the brain of the human subject and/or ii) slows cognitive or functional decline in the human subject.

69. The use of embodiment 68, wherein the reduction in Aβ deposits in the brain of the human subject is determined by amyloid PET brain imaging or a diagnostic that detects a biomarker for Aβ.

70. The use of embodiments 68 or 69, wherein the second dose of donanemab is administered to the human subject until there is about 20-100% reduction in Aβ deposits in the brain of the human subject.

71. The use of embodiment 70, wherein the Aβ deposits in the brain of the human subject are reduced by about 20%, about 25%, about 30%, about 35%, about 40%, about 45%, about 50%, about 75% or about 100%.

72. The use of embodiments 70 or 71, wherein the Aβ deposits in the brain of the patient are reduced by 100%.

73. The use of any one of embodiments 56 to 72, wherein the second dose of donanemab is administered to the human subject until the Aβ deposits in the brain of the human subject are reduced by i) about an average of about 25 centiloids to about 100 centiloids, ii) about an average of about 50 centiloids to about 100 centiloids, iii) about 100 centiloids, or iv) about 84 centiloids.

74. The use of any one of the embodiments 56 to 73, wherein the disease characterized by Aβ deposit in the brain of the human subject is selected from preclinical Alzheimer's disease, clinical Aβ, prodromal Aβ, mild Aβ, moderate Aβ, severe Aβ, Down's syndrome, clinical cerebral amyloid angiopathy, or pre-clinical cerebral amyloid angiopathy.

75. The use of any one of embodiments 56 to 74, wherein the human subject is an early symptomatic AD patient or wherein the human subject has prodromal AD or mild dementia due to AD.

76. The use of any one of embodiments 56 to 75, wherein the human subject has: i) very low to moderate tau burden or has been determined to have very low to moderate tau burden, ii) low to moderate tau burden or has been determined to have low to moderate tau burden, iii) very low to moderate tau burden or has been determined to have very low to moderate tau burden and one or two alleles of APOE e4, iv) low to moderate tau burden or has been determined to have low to moderate tau burden and one or two alleles of APOE e4, or v) one or two alleles of APOE e4.

77. The use of embodiment 76, wherein the human subject has i) very low to moderate tau burden if the tau burden as measured by PET brain imaging is ≤1.46 SUVr or ii) low to moderate tau burden if the tau burden as measured by PET brain imaging is from 1.10 SUVr to 1.46 SUVr.

78. The use of any one of embodiments 56-75, wherein the human subject i) does not have high tau burden or has been determined to not have a high tau burden or ii) carries one or two alleles of APOE e4 and does not have high tau burden or has been determined to not have a high tau burden.

79. The use of embodiment 78, wherein the human subject has high tau burden if the tau burden as measured by PET brain imaging is above 1.46 SUVr.

80. The use of embodiments 76 or 78, wherein the tau burden of the human subject is determined using tau PET brain imaging or a diagnostic that detects a biomarker for tau.

81. A method of treating or preventing a disease characterized by amyloid beta (Aβ) deposits in the brain of a human subject who has been determined to have i) very low to moderate tau burden or low to moderate tau burden or ii) very low to moderate tau burden or low to moderate tau burden and one or two alleles of APOE e4 comprising:
i) administering to the human subject one or more first doses of donanemab of about 100 mg to about 700 mg, wherein each first dose of donanemab is administered once about every 4 weeks; and
ii) 4 weeks after administering the one or more first doses, administering to the human subject one or more second doses of donanemab of greater than 700 mg to about 1400 mg, wherein each second dose is administered once about every 4 weeks; in simultaneous, separate, or sequential combination with an effective amount of Antibody 1.

82. A method of treating or preventing a disease characterized by amyloid beta (Aβ) deposits in the brain of a human subject comprising:
determining whether the human subject has tau burden in the temporal lobe, the occipital lobe, the parietal lobe, or the frontal lobe of the brain and if the human subject has tau burden in the temporal lobe, the occipital lobe, the parietal lobe, or the frontal lobe of the brain, then:
i) administering to the human subject one or more first doses of about 100 mg to about 700 mg of an anti-N3pGlu Aβ antibody, wherein each first dose is administered once about every four weeks; and ii) about four weeks after administering the one or more first doses, administering to the human subject one or more second doses of greater than 700 mg to about 1400 mg of an anti-N3pGlu Aβ antibody, wherein each second dose is administered once about every 4 weeks, in simultaneous, separate, or sequential combination with an effective amount of Antibody 1.

83. The method according to embodiment 82, wherein the human subject has tau burden in the posterolateral temporal lobe or the temporal lobe of the brain.

84. The method according to embodiment 82, wherein the human subject has tau burden in the occipital lobe of the brain.

85. The method according to embodiment 82, wherein the human subject has tau burden in the parietal lobe of the brain.

86. The method according to embodiment 82, wherein the human subject has tau burden in the frontal lobe of the brain.

87. The method according to embodiment 82, wherein the human subject has tau burden in the posterolateral temporal (PLT) and/or occipital lobe of the brain.

88. The method according to any one of embodiments 82-87, wherein the human subject has tau burden in i) parietal or precuneus region or ii) in frontal region along with tau burden in PLT or occipital regions of the brain.

89. The method according to any one of embodiments 82-86, wherein the human subject has tau burden i) isolated to frontal lobe or ii) in regions of the temporal lobe that do not include the posterolateral temporal region (PLT) of the brain.

90. The method according to any one of embodiments 82-88, wherein the human subject has tau burden in posterior-lateral temporal lobe, occipital lobe, and parietal lobe of the brain.

91. The method according to any one of embodiments 82-88, wherein the human subject has tau burden in posterior-lateral temporal lobe, occipital lobe, parietal lobe, and frontal lobe of the brain.

92. The method according to any one of embodiments 82-88, wherein the human subject has tau burden in posterior-lateral temporal lobe, occipital lobe, parietal lobe and/or frontal lobe of the brain.

93. The method according to any one of embodiments 82-92, wherein the human subject is administered the first dose once, two times, or three times before administering the second dose.

94. The method according to any one of embodiments 82-93, wherein the human subject is administered first doses of about 700 mg.

95. The method of any one of embodiments 82 to 94, wherein the human subject is administered one or more second doses of about 800 mg, about 900 mg, about 1000 mg, about 1100 mg, about 1200 mg, about 1300 mg, or about 1400 mg.

96. The method of any one of embodiments 82 to 95, wherein the human subject is administered one or more second doses of about 1400 mg.

97. The method of any one of embodiments 82 to 96, wherein the anti-N3pGlu Aβ antibody is administered to the human subject for a duration of up to 72 weeks or until normal level of amyloid is achieved.

98. The method of any one of embodiments 82 to 97, wherein the anti-N3pGlu Aβ antibody is administered to the human subject until the amyloid plaque level in the patient is about 25 centiloids or lower.

99. The method of any one of embodiments 82 to 98, wherein the anti-N3pGlu Aβ antibody is administered to the human subject until the amyloid plaque level in the human subject is about 25 centiloids or lower for two consecutive PET imaging scans, optionally, wherein the two consecutive PET imaging scans are at least 6 months apart, or about 11 centiloids or lower for one PET imaging scan.

100. The method of any one of embodiments 82 to 99, wherein the human subject is administered three first doses of 700 mg once every four weeks and then second doses of 1400 mg once every four weeks for a duration of up to 72 weeks.

101. The method of any one of embodiments 82 to 100, wherein the human subject is administered three first doses of 700 mg once every four weeks and then second doses of 1400 mg once every four weeks until the amyloid plaque level in the subject is about 25 centiloids or lower.

102. The method of any one of embodiments 82 to 101, wherein the human subject is administered three first doses of 700 mg once every four weeks and then second doses of 1400 mg once every four weeks until amyloid plaque level in the subject is about 25 centiloids or lower for two consecutive PET imaging scans, optionally, wherein the two consecutive PET imaging scans are at least 6 months apart, or about 11 centiloids or lower for one PET imaging scan.

103. The method of any one of embodiments 82 to 102, wherein the human subject is administered the second dose for a duration sufficient to treat or prevent the disease.

104. The method of any one of embodiments 82 to 103, wherein the treatment or prevention of the disease causes i) reduction in Aβ deposits in the brain of the human subject and/or ii) slows cognitive or functional decline in the human subject.

105. The method of embodiment 97, wherein the reduction in Aβ deposits in the brain of the human subject is determined by amyloid PET brain imaging or a diagnostic that detects a biomarker for Aβ.

106. The method of embodiments 97 or 98, wherein the second dose is administered to the human subject until there is about 20-100% reduction in Aβ deposits in the brain of the human subject.

107. The method of embodiment 106, wherein the Aβ deposits in the brain of the human subject are reduced by about 20%, about 25%, about 30%, about 35%, about 40%, about 45%, about 50%, about 75% or about 100%.

108. The method of any one of embodiments 82 to 107, wherein the second dose is administered to the human subject until the Aβ deposits in the brain of the human subject are reduced by i) about an average of about 25 centiloids to about 100 centiloids, ii) about an average of about 50 centiloids to about 100 centiloids, iii) about 100 centiloids, or iv) about 84 centiloids.

109. The method of any one of embodiments 82 to 108, wherein the disease characterized by Aβ deposit in the brain of the human subject is selected from preclinical Alzheimer's disease (AD), clinical Aβ, prodromal Aβ, mild Aβ, moderate Aβ, severe AD, Down's syndrome, clinical cerebral amyloid angiopathy, or pre-clinical cerebral amyloid angiopathy.

110. The method of any one of embodiments 82 to 109, wherein the human subject is an early symptomatic AD patient.

111. The method of embodiment 109, wherein the human subject has prodromal AD and mild dementia due to AD.
112. The method of any one of embodiments 82-111, wherein the human subject has: i) very low to moderate tau burden or has been determined to have very low to moderate tau burden, or ii) low to moderate tau burden or has been determined to have low to moderate tau burden.
113. The method of embodiment 112, wherein the human subject has i) very low to moderate tau burden if the tau burden as measured by PET brain imaging is ≤1.46 SUVr or ii) low to moderate tau burden if the tau burden as measured by PET brain imaging is from 1.10 SUVr to 1.46 SUVr.
114. The method of any one of embodiments 82 to 113, wherein the human subject does not have high tau burden or has been determined to not have a high tau burden.
115. The method of embodiment 114, wherein the human subject has high tau burden if the tau burden as measured by PET brain imaging is above 1.46 SUVr.
116. The method of embodiment 114 or 115, wherein the tau burden of the human subject is determined using PET brain imaging or a diagnostic that detects a biomarker for tau.
117. The method of any one of embodiments 82 to 116, wherein the anti-N3pGlu Aβ antibody comprises donanemab.
118. The method of any one of embodiments 82-117, wherein the patient has one or two alleles of APOE e4.
119. A method of decreasing/preventing further increase of tau burden or slowing the rate of tau accumulation in the temporal lobe, the occipital lobe, the parietal lobe, or the frontal lobe of a human brain comprising administering an anti-N3pGlu Aβ antibody to the human subject in simultaneous, separate, or sequential combination with an effective amount of Antibody 1.
120. A method of treating ARIA in a subject in need thereof, comprising administering to the subject a therapeutically effective amount of Antibody 1, or a pharmaceutical composition thereof.
121. A method of preventing ARIA in a subject in need thereof, comprising administering to the subject a therapeutically effective amount of Antibody 1, or a pharmaceutical composition thereof.

EXAMPLES

Figure 1:
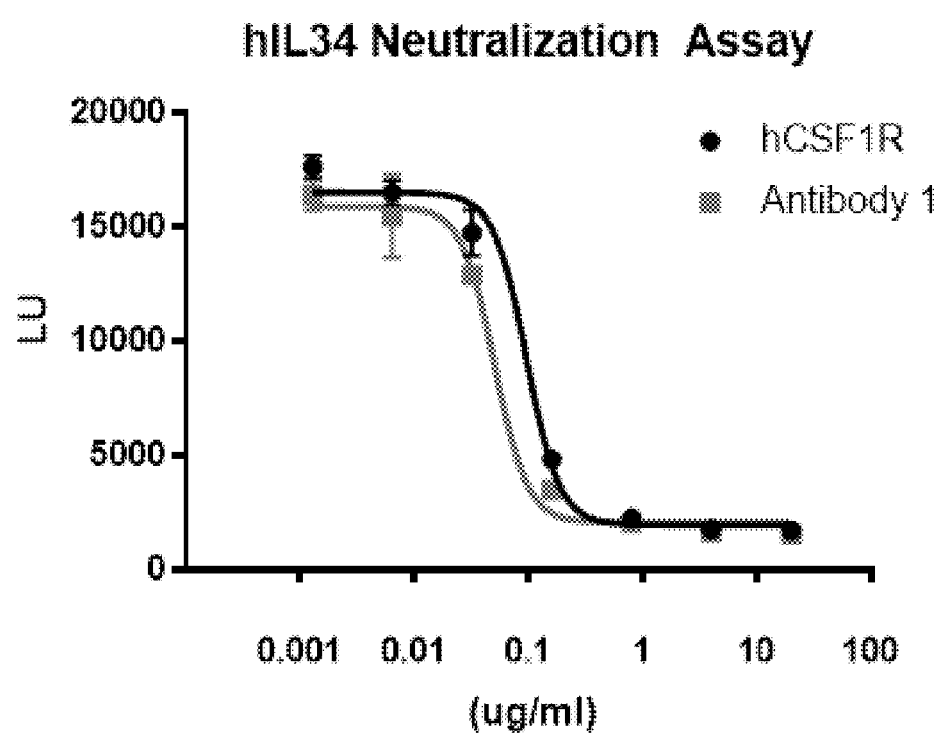
FIG. 1 shows Antibody 1 neutralization of human IL-34 induced luciferase reporter activity in hCSF1R expressing 293 SRE cells.

The following examples are offered to illustrate, but not to limit, the claimed invention. The results of the following assays demonstrate that exemplified monoclonal antibodies, such as Antibody 1, of the present disclosure bind and/or neutralize IL-34, and therefore may be used for treating immune-mediated and inflammatory diseases described herein.

Example 1: Antibody Generation, Expression and Purification

A panel of human anti-IL-34 antibodies are obtained using fully human yeast display libraries and screened to identify reagents that could be effective human IL-34 neutralizing antibodies. Mutations are systematically introduced into individual complementarity determining regions (CDRs) of each antibody and the resulting libraries are subjected to multiple rounds of selection with decreasing concentrations of antigen and/or increasing periods of dissociation, in order to isolate clones with improved affinities. The sequences of individual variants are determined and used to construct a combinatorial library which is subjected to an additional round of selection with increased stringency to identify additive or synergistic mutational pairings between the individual CDR regions. Individual combinatorial clones are sequenced, and binding characteristics are determined. In order to further increase the affinity to IL-34, these combinatorial clones may be subjected to additional rounds of single and combinatorial mutagenesis. This screening can be conducted against human or cyno IL-34 to increase affinity against a selected species. Selected antibodies can also be mutagenized to fix post-translational modifications such as isomerization, while retaining binding affinity to IL-34. Additionally, framework (FW) or CDR substitutions can be made to the antibody to revert sequences to their germline state in order to reduce potential immunogenicity risk.

Engineered and/or optimized anti-IL-34 antibodies, for instance referred to herein as Antibody 1, are obtained having the amino acid sequences of the variable regions of the heavy chain and light chain, and the complete heavy chain and light chain amino acid sequences, and the nucleotide sequences encoding the same, as listed below in the section entitled "Listing of Amino Acid and Nucleotide Sequences". The SEQ ID NO's corresponding to these sequences are shown in Table 1, as well as the light chain and heavy chain CDR amino acid sequences.

The exemplified anti-IL-34 antibodies of the present disclosure can be expressed and purified essentially as follows. An appropriate host cell, such as HEK 293, NS0 or CHO, can be either transiently or stably transfected with an expression system for secreting antibodies using an optimal predetermined HC:LC vector ratio (such as 1:3 or 1:2 or 1:1) or a single vector system encoding both the HC and the LC.

The expression plasmid contains, for example, DNA encoding the LC and HC of Antibody 1 (a DNA sequence of SEQ ID NO:11 encoding a HC of exemplified Antibody 1, and a DNA sequence of SEQ ID NO:12 encoding a LC amino acid sequence of exemplified Antibody 1); and are expressed from a commonly-used and suitable construct for this purpose. The clonally-derived cell lines are expanded and screened for Antibody 1 production, and a clonally-derived cell line is selected and established. This cell line is generated without any animal component-containing materials and used for production.

Clarified medium, into which the antibody is secreted, may be purified by conventional techniques, such as mixed-mode methods of ion-exchange and hydrophobic interaction chromatography. For example, the medium may be applied to and eluted from a Protein A or G column using conventional methods; mixed-mode methods of ion-exchange and hydrophobic interaction chromatography may also be used. Soluble aggregate and multimers may be effectively removed by common techniques, including size exclusion, hydrophobic interaction, ion exchange, or hydroxyapatite chromatography. An exemplified anti-IL-34 antibody of the present disclosure is concentrated and/or sterile filtered using common techniques. The purity of an exemplified antibody after these chromatography steps is greater than 95%. An exemplified anti-IL-34 antibody of the present disclosure may be immediately frozen at −70° C. or stored at 4° C. for several months.

Example 2: Characterization of the Anti-IL-34 Antibodies

Binding Affinity to Human and Cynomolgus Monkey IL-34 Binding affinity of anti-IL-34 monoclonal antibodies of the present disclosure to human and/or cynomolgus monkey (cyno) IL-34 may be determined by methods known in the art. Briefly, the binding affinity and kinetics of the antibody are evaluated by surface plasmon resonance using BIAcore™ 8K (Cytiva) at 37° C. The binding affinity is measured by immobilizing anti-IL-34 antibody on BIAcore™ Sensor Chip Protein A (Cytiva), and flowing human or cyno IL-34, starting from 25 nM or 12.5 nM in 2-fold serial dilution in HBS-EP+ buffer (Teknova). For each cycle, 200 µL IL-34 is flowed over the immobilized antibody at 100 µL/minute, and then dissociated for 20 minutes. The chip surface is regenerated with 50 µL of glycine buffer at pH 1.5 at a flow rate of 100 µL/minute. The data are fit to a 1:1 Langmiur binding mode to derive kon, koff and to calculate $K_D$. Table 3 shows the average of at least three experiments for human and cyno IL-34 for exemplified antibody 1.

TABLE 3

Binding affinity ($K_D$) of antibody-human and cyno IL-34 complexes at 37° C.

| Antibody | Antigen | Binding Affinity and Kinetics | | |
|---|---|---|---|---|
| | | Kon (1/Ms) | Koff (1/s) | $K_D$ (pM) |
| Exemplified Antibody 1 | Human | 6.6E+06 ± 3.8E+05 | 1.7E−04 ± 1.5E−05 | 25.9 ± 1.7 |
| Exemplified Antibody 1 | Cyno | 6.0E+06 ± 1.5E+06 | 1.8E−04 ± 1.6E−05 | 31.0 ± 5.9 |

Example 3: In Vitro Functional Characterization of the Anti-Human IL-34 Antibodies Antibodies of the present disclosure are tested for the ability to neutralize IL-34 binding and/or activity. Neutralization of IL-34 binding and/or activity by antibodies of the present disclosure may be assessed by one or more IL-34/CSF1R receptor binding assay formats, as well as IL-34 cell-based activity assays, for example, as described below.
Ability of Antibody 1 to Displace IL-34 from CSF1R Assays for neutralizing antibodies of IL-34/CSF1R binding may be done using an enzymatic assay. Such assays can use recombinantly expressed CSF1R extracellular domain proteins capable of binding to IL-34. These proteins can be bound to an ELISA plate in order to capture soluble IL-34. IL-34 can then be detected through either biotinylation of the antigen and detection via a streptavidin/neutravidin conjugated peroxidase or phosphatase enzyme. Such neutralization assays involve pre-incubation of the antibody being assessed with the labeled IL-34 (for example, for 1 hour) before addition to the binding assay (as well as control samples in which no antibody targeting IL-34 is involved).

CSF1R extracellular domain proteins (hCSF1R_Fc commercially available from R&D Cat #329-MR, cynomolgus CSF1R ECD-Fc (AAA is a linker between CSF1R extracellular domain and Fc) (SEQ ID NO: 34)) can be bound to an ELISA plate at concentrations of 30 nM in order to capture soluble biotinylated IL-34 and allowed to bind for one hour. After washing and blocking plate, biotinylated IL-34 may be added, then detected via streptavidin conjugated peroxidase. Concentrations of labeled IL-34 near the 80% binding level ($EC_{80}$) (3.7 nM) may be used in conjunction with a range of antibody concentrations (0-100 nM) to determine concentration of antibody required to displace IL-34 from CSF1R. After 1 hr incubation, IL-34 bound to CSF1R is detected via streptavidin conjugated peroxidase. The antibodies are assayed (n=2) and the average and standard deviation at each concentration are calculated. The potency of an antibody to displace IL-34 from CSF1R is reported as $IC_{50}$ (nM) with the calculated confidence interval (CI) in Table 4 and Table 5.

TABLE 4

Displacement of human IL-34 from human CSF1R

| Antibody 1 | human IL-34 bound to human CSF1R | |
|---|---|---|
| nM | Avg | Stdev |
| 100 | 0.1633 | 0.023 |
| 33 | 0.1676 | 0.076 |
| 11.1 | 0.1997 | 0.077 |
| 3.7 | 0.2703 | 0.117 |
| 1.2 | 0.1780 | 0.029 |
| 0.4 | 0.3116 | 0.044 |
| 0.14 | 0.8309 | 0.063 |
| 0.05 | 2.3993 | 0.010 |
| 0.02 | 3.1070 | 0.210 |
| 0.005 | 2.9406 | 0.032 |
| 0.002 | 2.9686 | 0.001 |
| 0.001 | 3.1566 | 0.113 |
| $IC_{50}$ (nM) | 0.07882 | |
| Confidence Interval | 0.06896 to 0.09007 | |

TABLE 5

Displacement of cyno IL-34 from cyno CSF1R

| Antibody 1 | cyno IL-34 bound to cyno CSF1R | |
|---|---|---|
| nM | Avg | Stdev |
| 100 | 0.1730 | 0.054 |
| 33 | 0.1578 | 0.033 |
| 11.1 | 0.1813 | 0.033 |
| 3.7 | 0.2183 | 0.021 |
| 1.2 | 0.3055 | 0.042 |
| 0.4 | 0.6367 | 0.058 |
| 0.14 | 1.5441 | 0.133 |
| 0.05 | 1.6924 | 0.100 |
| 0.02 | 1.8093 | 0.166 |
| 0.005 | 1.6164 | 0.168 |
| 0.002 | 1.5831 | 0.008 |
| 0.001 | 1.7761 | 0.024 |
| $IC_{50}$ (nM) | 0.2996 | |
| Confidence Interval | 0.2405 to 0.3731 | |

IL-34 binds to human CSF1R at approximately 50-100 pM affinity, necessitating a high-affinity antibody for effective neutralization of this cytokine in the CNS. The results in Table 4 show that Antibody 1 possesses high affinity for human IL-34 and can displace IL-34 from human CSF1R with an $IC_{50}$ of 0.07882 nM. The results in Table 4 show that Antibody 1 possesses high affinity for human IL-34, and in particular, Antibody 1 shows an affinity for human IL-34 comparable to hCSF1R, and thus possesses binding properties that enable them to effectively neutralize IL-34 in vivo. Blocking IL-34 is believed to provide a useful means for disease modification while avoiding safety concerns associated with some existing immunomodulatory therapies. Therefore, neutralizing IL-34-mediated signaling represents a therapeutic approach for the management of neuroinflammation, microgliosis and neurodegenerative diseases, such as Alzheimer's Disease and other tauopathies and inflammatory diseases. (See, e.g., Lelios, I. et al. Emerging roles of IL-34 in health and disease, *J Exp Med* (2020) 217 (3): e20190290).

Ability of Antibody 1 to Neutralize the Dimerization of CSF1R in the PathHunter® eXpress Dimerization Assay:

Human IL-34 neutralization can further be assessed by plating U2OS CSF1R/CSF1R cells (Path Hunter® eXpress Dimerization Assay, DiscoverX) in 96-well plates to assess the ability of anti-IL-34 antibodies to inhibit the dimerization of CSF1R. These assays utilize Enzyme Fragment Complementation (EFC) technology, where the b-galactosidase (b-gal) enzyme is split into two fragments, ProLink (PK) and Enzyme Acceptor (EA). Independently these fragments have no b-gal activity; however, when forced to complement through protein-protein interactions, they form an active b-gal enzyme. The PathHunter® eXpress Dimerization assay detects ligand-induced dimerization of two subunits of the CSF1R receptor-dimer pair. The cells have been engineered to co-express one CSF1R receptor subunit fused to Enzyme Donor (ED), and a second CSF1R dimer partner fused to Enzyme Acceptor (EA). Binding of human IL-34 to one receptor subunit induces it to interact with its dimer partner, forcing complementation of the two enzyme fragments. This results in the formation of a functional enzyme that hydrolyzes a substrate to generate a chemiluminescent signal. The reduction in relative fluorescence units (RFUs) shown in Table 6 reflects the ability of Antibody 1 to neutralize human IL-34 and reduce chemiluminescence. The half maximum inhibitory concentration ($IC_{50}$) value for Antibody 1 is 1.035 nM. Human CSF1R-Fc is used as a positive control in this assay and inhibits RFU units with an $IC_{50}$ of 1.025 nM. The data in Table 6 support the ability of the Antibody 1 to block the interaction of human IL-34 with CSF1R, thereby inhibiting the dimerization of CSF1R in this assay. This data supports the use of the antibodies of the present disclosure to neutralize human IL-34.

TABLE 6

Ability of Antibody 1 to neutralize the dimerization of the CSF1R in the PathHunter ® eXpress Dimerization Assay

| | hCSF1R-Fc | | Antibody 1 | |
| --- | --- | --- | --- | --- |
| Conc [nM] | Avg RLU | Standard deviation | Avg RLU | Standard deviation |
| 0.546329 | 141750 | 20954.54 | 143149.3 | 9354.359 |
| 1.092657 | 143284.3 | 20595.3 | 118715.3 | 4747.809 |
| 2.185315 | 144715.3 | 25275.37 | 129736.3 | 16011.77 |
| 4.370629 | 143242 | 28247.42 | 134560.3 | 11616.16 |
| 8.741259 | 57958.75 | 3264.96 | 44840.33 | 6203.152 |
| 17.48252 | 28603.25 | 5328.141 | 24513.67 | 4104.652 |
| 34.96503 | 27502 | 3611.769 | 20570.33 | 896.7309 |
| 69.93007 | 33178.5 | 4226.004 | 24025 | 4493.348 |
| 139.8601 | 27519.5 | 5065.463 | 21793 | 1757.859 |
| 279.7203 | 30378.5 | 6216.018 | 28330.33 | 3597.572 |
| $IC_{50}$ (nM) | 1.025 | | 1.035 | |

Inhibition of IL-34 Induced Responses In Vitro

Neutralization of IL-34 activity by antibodies of the present disclosure may be assessed by one or more IL-34 cell-based assays, for example, as described below. The ability of antibodies of the present disclosure to neutralize human IL-34 induced luciferase reporter activity can be assessed in 293 hCSF1R SRE cells, transfected with cDNAs to express human CSF1R (accession: NP_001275634.1). For example, 293/SRE cells stably overexpressing human CSF1R (hCSF1R) are dissociated in 0.05% trypsin-PBS and plated at 70,000 cells per 100 ul in tissue culture-treated 96 well plates. The following day, growth media is removed, and cells are starved with DMEM-F12 (Dulbecco's Modified Eagle Medium: Nutrient Mixture F-12) supplemented with heat-inactivated 1% FBS (fetal bovine serum). 24 hr-post starve, cells are treated with 100 ng/ml human IL-34 and multiple concentrations of either hCSF1R-Fc or Antibody 1 for 6 hr. Following incubation, cells are lysed with 50 ul Promega™ Glo™ Lysis Buffer (Promega™ E266A) for 5 minutes with gentle agitation. 50 ml of BrightGlo™ luminescence reagent (Promega™ E2620) is added and incubated on lysed cells for 2 minutes. Luminescence is read on Perkin Elmer Wallac 1420 Victor2™ Microplate Reader. The reduction in relative fluorescence units (RFUs) shown in Table 7, and FIG. 1, reflects the ability of Antibody 1 to neutralize human IL-34 induced luciferase activity. The half-maximum inhibitory concentration ($IC_{50}$) value for Antibody 1 is 0.05037 ug/ml for neutralization of hIL-34. Human CSF1R-Fc is used as a positive control in this assay and inhibits luciferase activity with an $IC_5n$ of 0.09603 ug/ml.

TABLE 7

Neutralization of human IL-34 induced luciferase reporter activity in hCSF1R expressing 293 SRE cells

| | hCSF1R | | Antibody 1 | |
| --- | --- | --- | --- | --- |
| Concentration [ug/ml] | Avg LU | Standard deviation | Avg LU | Standard deviation |
| 20 | 1691 | 77.782 | 1543 | 9.899 |
| 4.000 | 1737 | 180.312 | 1604 | 63.640 |
| 0.800 | 2244 | 154.856 | 2024 | 14.142 |
| 0.160 | 4819 | 53.033 | 3474 | 80.610 |
| 0.032 | 14728.5 | 1003.385 | 12877 | 186.676 |
| 0.006 | 16495 | 544.472 | 15464.5 | 1830.699 |
| 0.001 | 17608.5 | 478.711 | 16380 | 638.517 |
| $IC_{50}$ (ug/ml) | 0.09603 | | 0.05037 | |
| CI (ug/ml) | 0.06301 to 0.1464 | | 0.03634 to 0.06981 | |
| Positive Control (+) IL34 | 16903.33 | 2169.549 | | |
| Negative Control (−) IL34 | 3502 | 344.114 | | |

Figure 2:
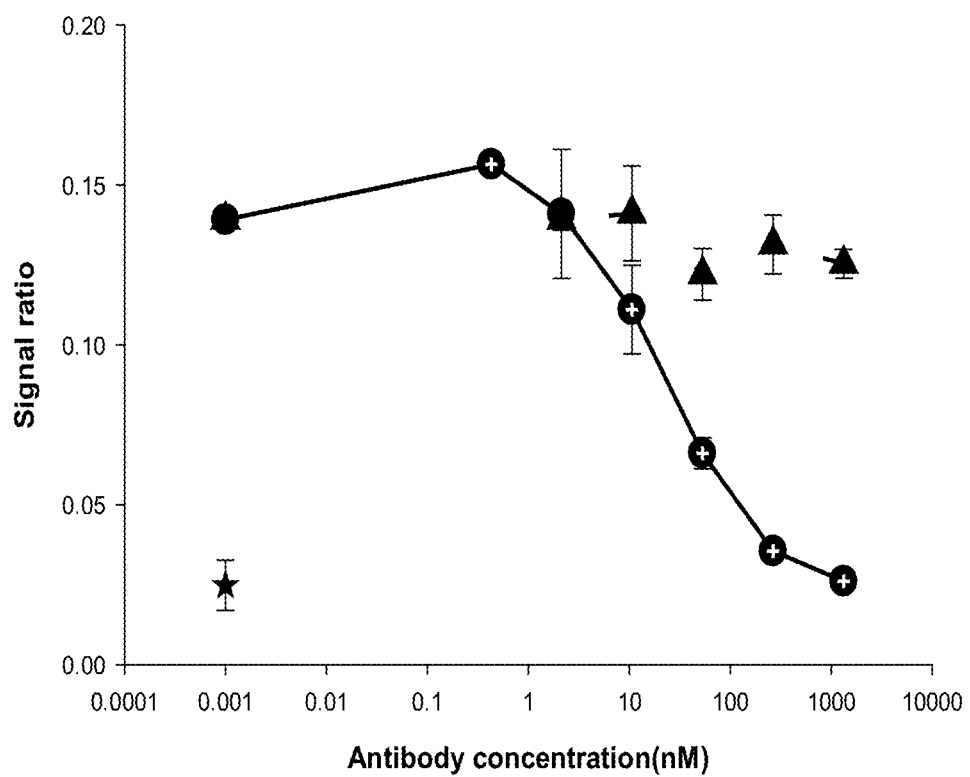
FIG. 2 shows the ability of Antibody 1 to inhibit ERK phosphorylation in NIH-3T3/CSF1R cells. Triangles represent cells treated with an isotype control antibody, circles represent cells treated with Antibody 1, and the star represents no IL-34 added to the assay (assay baseline).

Ability of Anti-IL-34 Antibodies to Inhibit ERK Phosphorylation in NIH-3T3/CSF1R Cells:

IL-34 neutralization can be determined by assessing the ability of anti-IL-34 antibodies to inhibit extracellular-signal-regulated kinase (ERK) phosphorylation in NIH-3T3/CSF1R. In this assay, cells are plated on day 1 in DMEM supplemented with 10% FBS and incubated overnight at 37° C. On day 2, medium is removed, cells are washed in serum-free DMEM and incubated for an additional 24-hour period. On the third day, the medium is replaced with serum-free DMEM containing anti-IL-34 antibody. Human or cynomolgus IL-34 is added for 5 minutes to the final concentration of 1 ug/ml. Either human or cynomolgus IL-34 and an isotype control antibody serve as positive and negative controls, respectively. Phospho/Total ERK1/2 levels are assessed by measuring electrochemiluminescence signal using the Whole Cell Lysate Kit (Meso Scale Discovery, cat #K15107D). The data is calculated as a ratio of electrochemiluminescence signal for phospho-ERK1/2 versus total ERK1/2 protein. The reduction in the signal ratio shown in Table 8 and/or FIG. 2, reflects the ability of Antibody 1 to neutralize IL-34 activity. The half-maximum inhibitory concentration ($IC_{50}$) value for Antibody 1 against human IL-34 is 26 nM, and against cynomolgus IL-34 is 53 nM.

TABLE 8

Ability of Antibody 1 to inhibit human IL34-driven ERK phosphorylation in NIH-3T3/CSF1R cells

| Concentration (nM) | Signal Ratio | Standard Deviation |
|---|---|---|
| 0 | 0.139165 | 0.003242 |
| 0.43 | 0.156491 | 5.86E−05 |
| 2.13 | 0.141003 | 0.020171 |
| 10.64 | 0.111073 | 0.013866 |
| 53.2 | 0.066085 | 0.004829 |
| 266 | 0.035514 | 0.001473 |
| 1330 | 0.026086 | 0.000562 |
| $IC_{50}$ (nM) | 26 | |

TABLE 9

Ability of Antibody 1 to inhibit cynomolgus IL34-driven ERK phosphorylation in NIH-3T3/CSF1R cells

| Concentration (nM) | Signal Ratio | Standard Deviation |
|---|---|---|
| 0 | 0.120146 | 0.00083 |
| 0.43 | 0.122052 | 0.011009 |
| 2.13 | 0.127126 | 0.000818 |
| 10.64 | 0.12391 | 0.004007 |
| 53.2 | 0.091267 | 0.007267 |
| 266 | 0.052691 | 0.002386 |
| 1330 | 0.049513 | 0.003252 |
| $IC_{50}$ (nM) | 53 | |

Ability of Anti-IL34 Antibodies to Inhibit IL-34 Induced Expression of CD163 in Human Monocytes by Flow Cytometry:

IL-34 neutralization can also be assessed by measuring the expression of the cell surface antigen CD163 in human monocytes after treatment with IL-34 by flow cytometry (See for example, Boulakirba, S., et al. *IL-34 and CSF-1 display an equivalent macrophage differentiation ability but a different polarization potential. Sci Rep* 8, 256 (2018). CD14-positive monocytes are treated with IL-34 for 6 days and CD163 expression is assessed by flow cytometry after staining with antibodies for CD163. In the experiments a change in the number of cells expressing CD163 indicates that IL-34 treatment increases the expression of this antigen in monocytes. The increase in CD163 expression is inhibited by the addition of Antibody 1. An isotype matched IgG4 antibody is used as a negative control in this experiment. The results are shown in Table 10.

CD14+ human monocytes may differentiate into macrophages with addition of IL-34 (100 ng/ml). Macrophage marker CD163 can be used to monitor extent of differentiation. This differentiation to macrophages may be inhibited by addition of anti-IL-34 antibodies. CD14+ human monocytes are plated in 6 well plates with or without IL-34. Cells are treated with anti-IL-34 antibodies, for instance Antibody 1, or IgG4 PAA at 15 ug/ml for a total of 6 days, with treatment refreshed at day 3. On day 6 cells are removed from plate with non-enzymatic cell dissociation buffer, collected and washed in FACS buffer (PBS+2% FBS+0.1% sodium azide+2% EDTA). Cells are blocked for 30 minutes with TruStain FcX (Cat #422302) at manufacturer recommendation. Following blocking, cells are washed in FACS buffer and stained with anti-CD163-PE or IgGk Isotype control-PE for 1 hr at 4 C. At end of incubation, cells are washed, and flow analysis performed on Accuri using minimum of 10,000 events. Median-PE-A levels are collected for each treatment.

TABLE 10

Inhibition of IL-34 induced expression of CD163 in human monocytes by flow cytometry

| Treatment | IgG stain (Mean PE-A) | CD163 stain (Mean PE-A) |
|---|---|---|
| (−) IL-34 | 7,750.56 | 130,783.14 |
| (+) IL-34 | 5,204.62 | 1,245,847.72 |
| (+)IL-34 and Antibody 1 (15 ug/ml) | 5,693.60 | 104,350.32 |
| (+)IL-34 and IgG4 PAA (15 ug/ml) | 6,011.43 | 715,201.30 |
| Unstained Cells | 2,622.87 | |

The inhibition by Antibody 1 of CD163 expression in human monocytes, in response to IL-34, demonstrates the ability of the antibodies of the present disclosure to modulate monocyte/macrophage number and/or phenotypic differentiation responses to IL-34, and supports the use of the present antibodies to treat immune-mediated diseases, such as neuroinflammation and other inflammatory conditions (See, e.g., Lelios, I. et al. *Emerging roles of IL-34 in health and disease, J Exp Med* (2020) 217 (3): e20190290).

Example 4: Characterization of Antibody 1 Immunogenicity Potential Dendritic Cell (DC) Internalization Assay Monocyte-Derived DC Culturing (MDDC)

CD14+ monocytes are isolated from periphery blood mononuclear cells (PBMCs) and are cultured and differentiated into DC following standard protocols. Briefly, PBMCs are isolated using density-gradient centrifugation with Ficoll (#17-1440-02, GE Healthcare) and Sepmate 50 (#15450, STEMCELL Technologies) from LRS-WBC. CD14+ monocytes are isolated using positive selection with a CD14+ microbead kit (#130-050-201, Miltenyi Biotec) following the manufacturer's manual. Cells are then cultured at 1 million/ml with 1000 unit/ml GM-CSF and 600 unit/ml IL-4 for 6 days to drive to immature dendritic cells (MDDC) in RPMI medium with L-glutamine and 25 mM HEPES supplemented with 10% FBS, 1 mM sodium pyruvate, 1×penicillin-streptomycin, 1×non-essential amino acids, and 55 µM 2-mercaptoethanol (hereafter referred to complete RPMI medium or medium, purchased from Life Technologies). The medium is changed twice, on day 2 and day 5. On day 6, cells are gently collected with a cell scraper and used for experiment. MDDC are characterized visually for dendritic morphology by microscope and for expression of CD14, CD1 Ic, and HLA-DR by flow cytometry. Their ability to respond to LPS treatment is confirmed by measuring upregulation of CD80, CD83, and CD86 using flow cytometry.

Conjugation of Fab-TAMRA-QSY7

A F(ab')2 fragment goat anti-human IgG (Jackson ImmunoResearch) is double-labeled with QSY7-NHS and TAMRA-SE (Molecular Probes) to obtain Fab-TAMRA-QSY7 used as a universal probe to track test article internalization. Each vial of F(ab')2 (approximately 1 ml at 1.3 mg/ml) is concentrated to about 2 mg/ml by centrifugation at 14,000 rcf for 2 minutes with the Amico Ultra-0.5 centrifugal filter device (#UFC501096, Millipore). The pH is adjusted to basic (>pH 8) with 10% (v/v) 1 M sodium bicarbonate, and 6.8 µl QSY-NHS stock solution at 10 mM in DMSO is added and mixed. The reaction vial is kept in dark at room temperature for 30 min. The intermediate product, Fab-QSY7, is purified with Zeba Spin desalting column (#89890, Thermo Scientific) by centrifugation at 1000 relative centrifugal force (RCF) for 2 min. The concentration and degree of labeling (DOL) are calculated by measuring the absorbance at 280 nm and 560 nm on a NanoDrop (ThermoFisher). Fab-QSY7 is then concentrated to about 2 mg/ml by centrifugation at 14,000 rcf for 2 min with Amico Ultra-0.5 centrifugal filter device again. After pH adjustment with 10% (v/v) 1 M sodium bicarbonate, 4.3 µl of 15 mM TAMRA-SE stock solution in DMSO are added and mixed. After 30 min. at room temperature in the dark, the final product Fab-TAMRA-QSY7 is purified and collected using a Zeba Spin desalting column by centrifugation at 1000 ref for 2 min. The concentration and DOL are again quantitated by reading the absorbance at 280 nm, 555 nm, and 560 nm on a NanoDrop Spectrophotometer. Using this protocol, about 300 µl of Fab-TAMRA-QSY7 at around 1.5 mg/ml with approximately two QSY7 and two TAMRA per F(ab')2 are obtained.

Standardized Internalization Study by FACS

Individual test molecules are normalized to 1 mg/ml with PBS and then further diluted to 8 µg/ml in complete RPMI medium. Fab-TAMRA-QSY7 is diluted to 5.33 µg/ml in complete RPMI medium. The antibody and Fab-TAMRA-QSY7 are mixed with equal volume and incubated for 30 min at 4° C. in dark for complex formation. MDDC are resuspended at 4 million/ml in complete RPMI medium and seeded at 50 µl per well in a 96-well round-bottom plate, to which 50 µl of the antibody/probe complex is added. Cells are incubated for 24 h at 37° C. in a $CO_2$ incubator. Cells are washed with 2% FBS PBS and resuspended in 100 µl 2% FBS PBS with Cytox Green live/dead dye. Data are collected on a BD LSR Fortessa X-20 and analyzed in FlowJo. Live single cells are gated and percent of TAMRA fluorescence positive cells is recorded as the readout.

Data Presentation and Statistical Analysis

Molecules are tested on three or more donors in duplicate or triplicate. The percent of TAMRA-positive population is considered for each donor. To allow the comparison of molecules with data generated from different donors, a normalized internalization index (NII) is used. The internalization signal is normalized to IgG1 isotype (NII=0) and an internal positive control PC (NII=100) using the formula:

$$100 \times \frac{X_{TAMRA} - IgG1\ isotype_{TAMRA}}{PC_{TAMRA} - IgG1\ isotype_{TAMRA}}$$

where $X_{TAMRA}$, $IgG1\ isotype_{TAMRA}$, and $PC_{TAMRA}$ are the percent of TAMRA-positive population for the test molecule X, IgG1 isotype, and PC respectively. Data are analyzed in JMP® 14.1.0 or Graphpad Prism 8.1.2. Mean of the percent of TAMRA-positive population and NII are calculated and reported. Increased internalization in antigen presenting cells such as DCs is associated with increased immunogenicity risk. The geometric mean for duplicate experiments for Antibody 1 is shown in Table 11.

TABLE 11

DC internalization Results

| Test Antibody | Normalized Internalization Index |
|---|---|
| Antibody 1 | 53.2 |

(See e.g. Wen, Y., Cahya, S., Zeng, W. et al. Development of a FRET-Based Assay for Analysis of mAbs Internalization and Processing by Dendritic Cells in Preclinical Immunogenicity Risk Assessment. AAPS J 22, 68 (2020))

MAPPs Assay (MHC-Associated Peptide Proteomics) Methods:

Primary human dendritic cells from 10 normal human donors are prepared from buffy coats by isolation of CD-14 positive cells and differentiated into immature dendritic cells by incubation with 20 ng/ml IL-4 and 40 ng/ml GM-CSF in complete RPMI media containing 5% Serum Replacement (Thermo Fisher Scientific, cat #A2596101) for 3 days at 37° C. and 5% $CO_2$ as described (Knierman et al., "The Human Leukocyte Antigen Class II Immunopeptidome of the SARS-CoV-2 Spike Glycoprotein", Cell Reports, 33, 108454 (2020)). Three micromolar of test antibody is added to approximately $5 \times 10^6$ cells on day 4 and fresh media containing 5 µg/ml of LPS to transform the cells into mature dendritic cells is exchanged after 5-hour incubation. The matured cells are lysed in 1ml of RIPA buffer with protease inhibitors and DNAse the following day. The lysates are stored at −80° C. until sample analysis.

An automated liquid handling system is used to isolate the HLA-II molecules from thawed lysate using biotinylated anti-pan HLA class II antibody (clone Tu39). The bound receptor-peptide complex is eluted with 5% acetic acid, 0.1% TFA. The eluted MHC-II peptides are passed over a prewashed 10 k MWCO filter to remove high molecular weight proteins. The isolated MHC-II peptides are analyzed by nano LC/MS using a Thermo easy 1200 nLC-HPLC system with a Thermo LUMOS mass spectrometer. The separation used a 75 µm×7 cm YMC-ODS C18 column for 65-minute gradient with a 250 nL/min flow rate and 0.1% formic acid in water as A solvent and 80% acetonitrile with 0.1% formic acid as B solvent. Mass spectrometry is run in full scan mode with 240,000 resolution followed by a 3 second data dependent MS/MS cycle comprised of ion trap rapid scans with HCD and EThcD fragmentation.

Peptide identifications are generated by an internal proteomics pipeline (Higgs et al., "Label-free LC-MS method for the identification of biomarkers", Methods in Molecular Biology, 428, 209-230 (2008)) using multiple search algorithms with no enzyme search parameter against a bovine/human database containing the test antibody sequences. A KNIME workflow is used to process the identification files for the samples. Peptides identified from the test articles are aligned against the parent sequence. A summary is created for all donors that annotates the percent of donors that display non-germline residues, the number of different regions that display peptides with non-germline residues and the depth of peptide display at each region with non-germline residues. Increases in the extent of display of non-germline peptides is associated with increased risk for immunogenicity. Results for Antibody 1 are shown in Table 12.

TABLE 12

MAPPs Results

| Test Antibody | % Donors with non-germline cluster(s) | # Clusters with non-germline residue(s) |
|---|---|---|
| Antibody 1 | 66% (6/9) | 2 |

T Cell Proliferation Assay

This assay assesses the ability of test candidate or test candidate's MAPPs-derived peptide clusters to activate CD4+ T cells by inducing cellular proliferation as described (Walsh et al., "Post-hoc assessment of the immunogenicity of three antibodies reveals distinct immune stimulatory mechanisms", mAbs, 12, 1764829 (2020)). Cryopreserved PBMC's were used from 10 healthy donors and the CD8+ T cells were depleted from the PBMC's and labeled with 1 μM Carboxyfluorescein Diacetate Succinimidyl Ester (CFSE). PBMCs were seeded at 4×10⁶ cells/ml/well in AIM-V media (Life Technologies, cat #12055-083) containing 5% CTS™ Immune Cell SR (Gibco, cat #A2596101) and tested in triplicate in 2.0 mL containing the different test articles, DMSO control, media control, and keyhole limpet haemocyanin (KLH; positive control). Cells were cultured and incubated for 7 days at 37° C. with 5% $CO_2$. On day 7, samples were stained with the following cell surface markers: anti-CD3, anti-CD4, anti-CD14, anti-CD19, and DAPI for viability detection by flow cytometry using a BD LSR-Fortessa™ equipped with a High Throughput Sampler (HTS). Data was analyzed using FlowJo® Software (FlowJo, LLC, TreeStar) and a Cellular Division Index (CDI) was calculated. Briefly, the CDI for each test molecule was calculated by dividing the percent of proliferating $CFSE^{dim}CD4+$ T cells in the stimulated wells by the percent of proliferating $CFSE^{dim}CD4+$ T cells in the unstimulated wells. A CDI of ≥2.5 was considered to represent a positive response. A percent donor frequency across all donors was evaluated. Results for Antibody 1 are shown in Table 13.

TABLE 13

The Frequency of CD4+ T cell Responses

| Molecule Tested | % Positive Donors | Median CDI (Positive Donors) | Median CDI (All donors) | Range High | Range Low | Number of donors |
|---|---|---|---|---|---|---|
| Antibody 1 | 10 | 2.8 | 1.0 | 2.8 | 0.3 | 1/10 |

Example 5: Antibody Pharmacokinetics in Cynomolgus Monkey

Cynomolgus monkeys are administered a single 3 mg/kg intravenous (IV) dose of Antibody 1 in PBS (pH 7.4) in a volume of 1 mL/kg. For pharmacokinetic characterization, blood is collected from 2 animals/timepoint at 1, 3, 6, 24, 48, 72, 96, 120, 168, 240, 336, 408, 504 and 672 hours post dose and processed to serum. Serum concentrations of Antibody 1 are determined by a qualified immunoaffinity liquid chromatography mass-spectrometry method. Antibody 1 and a human antibody internal standard (stable isotope labeled human IgG) are extracted from 100% cynomolgus monkey serum using a biotinylated goat anti-human IgG antibody followed by quantifying a tryptic surrogate peptide using a Q-Exactive™ Orbitrap® mass spectrometer. Pharmacokinetic parameters are calculated using non-compartmental analysis (NCA) for each animal (N=2) and parameters are summarized by the mean value. NCA and summary statistic calculations are performed using Phoenix. As shown in Table 14, Antibody 1 demonstrates an extended pharmacokinetic profile in cynomolgus monkeys.

TABLE 14

Plasma Pharmacokinetic Parameters for Antibody 1 Following a Single 3 mg/kg IV Dose to Cynomolgus Monkeys.

| Route | Dose (mg/kg) | $C_0$ (μg/mL) | $AUC_{0-inf}$ (hr*μg/mL) | CL (mL/hr/kg) | Vss (mL/kg) | $t_{1/2}$ (hr) |
|---|---|---|---|---|---|---|
| IV | 3 | 77.2 | 14400 | 0.209 | 65.3 | 216 |

```
Listing of Amino Acid and Nucleotide Sequences

Heavy Chain of Antibody 1 (SEQ ID NO: 1)
EVQLLESGGGLVQPGGSLRLSCAASGFAFSNYAMSWVRQAPGKGLEWVSAISAS
GGKTYYADSVKGRFTISRDNSKNTLYLQMNSLRAEDTAVYYCAKRGYLWHAFD
HWGRGTLVTVSSASTKGPSVFPLAPCSRSTSESTAALGCLVKDYFPEPVTVSWNS
GALTSGVHTFPAVLQSSGLYSLSSVVTVPSSSLGTKTYTCNVDHKPSNTKVDKRV
ESKYGPPCPPCPAPEAAGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNK
GLPSSIEKTISKAKGQPREPQVYTLPPSQEEMTKNQVSLTCLVKGFYPSDIAVEWE
SNGQPENNYKTTPPVLDSDGSFFLYSRLTVDKSRWQEGNVFSCSVMHEALHNHY
TQKSLSLSLG Light Chain of Antibody 1 (SEQ ID NO: 2)
EIVLTQSPGTLSLSPGERATLSCRASQSVSSLYLAWYQQKPGQAPRLLIYGASSRA
TGIPDRFSGSGSGTDFTLTISRLEPEDFAVYYCQVVGSSPPFTFGGGTKVEIKRTVA
APSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC HCVR of Antibody 1 (SEQ ID NO: 3)
EVQLLESGGGLVQPGGSLRLSCAASGFAFSNYAMSWVRQAPGKGLEWVSAISAS
GGKTYYADSVKGRFTISRDNSKNTLYLQMNSLRAEDTAVYYCAKRGYLWHAFD
H LCVR of Antibody 1 (SEQ ID NO: 4)
EIVLTQSPGTLSLSPGERATLSCRASQSVSSLYLAWYQQKPGQAPRLLIYGASSRA
TGIPDRFSGSGSGTDFTLTISRLEPEDFAVYYCQVVGSSPPFT
```

| Listing of Amino Acid and Nucleotide Sequences |
| --- |

HCDR1 of Antibody 1 (SEQ ID NO: 5)
AASGFAFSNYAMS

HCDR2 of Antibody 1 (SEQ ID NO: 6)
AISASGGKTY

HCDR3 of Antibody 1 (SEQ ID NO: 7)
AKRGYLWHAFDH

LCDR1 of Antibody 1 (SEQ ID NO: 8)
RASQSVSSLYLA

LCDR2 of Antibody 1 (SEQ ID NO: 9)
YGASSRAT

LCDR3 of Antibody 1 (SEQ ID NO: 10)
QVVGSSPPFT

DNA Encoding the Heavy Chain of Antibody 1 (SEQ ID NO: 11)
gaagtccagttgctggaatctggcggcggtctcgttcagccaggggggcagcttgcgtcttagttgtgcagcatccgggtttgcctt
ttccaattacgctatgtcatgggtaaggcaagccccaggcaaaggactcgaatgggtttccgccattagtgcctcaggaggcaag
acatactatgccgattctgtaaagggcagatttactatatctcgggacaattctaaaaatacactctatcttcagatgaatagccttag
agctgaagataccgctgtctactactgtgccaaacgtggctacctttggcacgcctttgatcactgggtcggggtactctcgtaac
tgtaagctccgcctccaccaagggcccatcggtcttcccgctagcgccctgctccaggagcacctccgagagcacagccgccc
tgggctgcctggtcaaggactacttccccgaaccggtgacggtgtcgtggaactcaggcgccctgaccagcggcgtgcacacc
ttcccggctgtcctacagtcctcaggactctactccctcagcagcgtggtgaccgtgccctccagcagcttgggcacgaagacct
acacctgcaacgtagatcacaagcccagcaacaccaaggtggacaagagagttgagtccaaatatggtccccatgccaccc
tgcccagcacctgaggccgccggggaccatcagtcttcctgttcccccaaaacccaaggacactctcatgatctcccggacc
cctgaggtcacgtgcgtggtggtggacgtgagccaggaagaccccgaggtccagttcaactggtacgtggatggcgtggaggt
gcataatgccaagacaaagccgcgggaggagcagttcaacagcacgtaccgtgtggtcagcgtcctcaccgtcctgcaccag
gactggctgaacggcaaggagtacaagtgcaaggtctccaacaaaggcctcccgtcctccatcgagaaaaccatctccaaagc
caaagggcagccccgagagccacaggtgtacaccctgccccccatcccaggaggagatgaccaagaaccaggtcagcctgac
ctgcctggtcaaaggcttctaccccagcgacatcgccgtggagtgggaaagcaatgggcagccggagaacaactacaagacc
acgcctcccgtgctggactccgacggctccttcttcctctacagcaggctaaccgtggacaagagcaggtggcaggaggggaa
tgtcttctcatgctccgtgatgcatgaggctctgcacaaccactacacacagaagagcctctccctgtctctgggt DNA Encoding the Light Chain of Antibody 1 (SEQ ID NO: 12)
gaaatagttctcactcagtccctgggacactctccctgagtccaggagaacgtgcaacactcagttgccgtgcaagccagtccg
tctcatccttgtatcttgcttggtaccaacaaaaacctggacaggccccgtcttcttatctatggtgcctccagtcgcgcaactgg
tattcccgaccggttcagcggcagtgggtccggcactgacttcaccctgactataagtcggttggagccagaggactttgccgtg
tactattgccaagtggtgggaagctcccctccttcactttcggccggagggaccaaggtagaaatcaaaagaactgtggcggcg
ccatctgtcttcatcttcccgccatctgatgagcagttgaaatccggaactgcctctgttgtgtgcctgctgaataacttctatcccag
agaggccaaagtacagtggaaggtggataacgccctccaatcgggtaactcccaggagagtgtcacagagcaggacagcaa
ggacagcacctacagcctcagcagcaccctgacgctgagcaaagcagactacgagaaacacaaagtctacgcctgcgaagtc
acccatcagggcctgagctcgcccgtcacaaagagcttcaacaggggagagtgc HCDR1 of Antibody 1 (Kabat) (SEQ ID NO: 13)
NYAMS HCDR2 of Antibody 1 (Kabat) (SEQ ID NO: 14)
AISASGGKTYYADSVKG HCDR3 of Antibody 1 (Kabat) (SEQ ID NO: 15)
RGYLWHAFDH LCDR1 of Antibody 1 (Kabat) (SEQ ID NO: 16)
RASQSVSSLYLA LCDR2 of Antibody 1 (Kabat) (SEQ ID NO: 17)
GASSRAT LCDR3 of Antibody 1 (Kabat) (SEQ ID NO: 18)
QVVGSSPPFT HCDR1 of Antibody 1 (Chothia) (SEQ ID NO: 19)
GFAFSNY HCDR2 of Antibody 1 (Chothia) (SEQ ID NO: 20)
SASGGK HCDR3 of Antibody 1 (Chothia) (SEQ ID NO: 21)
RGYLWHAFDH LCDR1 of Antibody 1 (Chothia) (SEQ ID NO: 22)
RASQSVSSLYLA

| Listing of Amino Acid and Nucleotide Sequences |
| --- |

LCDR2 of Antibody 1 (Chothia) (SEQ ID NO: 23)
GASSRAT

LCDR3 of Antibody 1 (Chothia) (SEQ ID NO: 24)
QVVGSSPPFT

HCDR1 of Antibody 1 (IMGT) (SEQ ID NO: 25)
GFAFSNYA

HCDR2 of Antibody 1 (IMGT) (SEQ ID NO: 26)
ISASGGKT

HCDR3 of Antibody 1 (IMGT) (SEQ ID NO: 27)
AKRGYLWHAFDH

LCDR1 of Antibody 1 (IMGT) (SEQ ID NO: 28)
QSVSSLY

LCDR2 of Antibody 1 (IMGT) (SEQ ID NO: 29)
GAS

LCDR3 of Antibody 1 (IMGT) (SEQ ID NO: 30)
QVVGSSPPFT

Human IL-34 (SEQ ID NO: 31)
NEPLEMWPLTQNEECTVTGFLRDKLQYRSRLQYMKHYFPINYKISVPYEGVFRIA
NVTRLQRAQVSERELRYLWVLVSLSATESVQDVLLEGHPSWKYLQEVETLLLNV
QQGLTDVEVSPKVESVLSLLNAPGPNLKLVRPKALLDNCFRVMELLYCSCCKQS
SVLNWQDCEVPSPQSCSPEPSLQYAATQLYPPPPWSPSSPPHSTGSVRPVRAQGE
GLLP IgG4PAA hinge region (SEQ ID NO: 32)
ESKYGPPCPPCP IgG4PAA Fc region (SEQ ID NO: 33)
APEAAGGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYK
TTPPVLDSDGSFFLYSRLTVDKSRWQEGNVFSCSVMHEALHNHYTQKSLSLSLG Sequence of cynomolgus CSF1R ECD-Fc (SEQ ID NO: 34)
IPVIEPSGPELVVKPGETVTLRCVGNGSVEWDGPISPHWTLYSDGPSSVLTTNNAT
FQNTRTYRCTEPGDPLGGSAAIHLYVKDPARPWNVLAKEVVVFEDQDALLPCLL
TDPVLEAGVSLVRLRGRPLLRHTNYSFSPWHGFIIHRAKFIQGQDYQCSALMGGR
KVMSISIRLKVQKVIPGPPALTLVPAELVRIRGEAAQIVCSASNIDVDFDVFLQHNT
TKLAIPQRSDFHDNRYQKVLTLSLGQVDFQHAGNYSCVASNVQGKHSTSMFFRV
VESAYLDLSSEQNLIQEVTVGEGLNLKVMVEAYPGLQGFNWTYLGPFSDHQPEP
KLANATTKDTYRHTFTLSLPRLKPSEAGRYSFLARNPGGWRALTFELTLRYPPEV
SVIWTSINGSGTLLCAASGYPQPNVTWLQCAGHTDRCDEAQVLQVWVDPHPEVL
SQEPFQKVTVQSLLTAETLEHNQTYECRAHNSVGSGSWAFIPISAGARTHPPDEA
AAEPKSSDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHE
ALHNHYTQKSLSLSP Heavy Chain of Antibody 2 (SEQ ID NO: 35)
EVQLLESGGGLVQPGGSLRLSCAASGFAFSNYAMSWVRQAPGKGLEWVSAISAS
GGKTYYADSVKGRFTISRDNSKNTLYLQMNSLRAEDTAVYYCAKRGYLWHAFD
HWGRGTLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKRV
EPKSCDKTHTCPPCPAPEAEGAPSVFLFPPKPKDTLMISRTPEVTCVVVDVSHEDP
EVKFNWYVDGVEVHNAKTKPREEQYNSTYRVVSVLTVLHQDWLNGKEYKCKV
SNKALPSSIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVMHEALH
NHYTQKSLSLSPGK Heavy Chain of Antibody 3 (SEQ ID NO: 36)
EVQLLESGGGLVQPGGSLRLSCAASGFAFSNYAMSWVRQAPGKGLEWVSAISAS
GGKTYYADSVKGRFTISRDNSKNTLYLQMNSLRAEDTAVYYCAKRGYLWHAFD
HWGRGTLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMHEALH
NHYTQKSLSLSPG Listing of Amino Acid and Nucleotide Sequences Heavy Chain of Antibody 4 (SEQ ID NO: 37)
EVQLLESGGGLVQPGGSLRLSCAASGFAFSNYAMSWVRQAPGKGLEWVSAISAS
GGKTYYADSVKGRFTISRDNSKNTLYLQMNSLRAEDTAVYYCAKRGYLWHAFD
HWGRGTLVTVSSASTKGPSVFPLAPCSRSTSESTAALGCLVKDYFPEPVTVSWNS
GALTSGVHTFPAVLQSSGLYSLSSVVTVPSSNFGTQTYTCNVDHKPSNTKVDKTV
ERKCCVECPPCPAPPVAGPSVFLFPPKPKDTLMISRTPEVTCVVVDVSHEDPEVQF
NWYVDGVEVHNAKTKPREEQFNSTFRVVSVLTVVHQDWLNGKEYKCKVSNKG
LPAPIEKTISKTKGQPREPQVYTLPPSREEMTKNQVSLTCLVKGFYPSDIAVEWES
NGQPENNYKTTPPMLDSDGSFFLYSKLTVDKSRWQQGNVFSCSVMHEALHNHY
TQKSLSLSPG Heavy Chain of donanemab (SEQ ID NO: 38)
QVQLVQSGAEVKKPGSSVKVSCKASGYDFTRYYINWVRQAPGQGLEWMGWINP
GSGNTKYNEKFKGRVTITADESTSTAYMELSSLRSEDTAVYYCAREGITVYWGQ
GTTVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKS
CDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHY
TQKSLSLSPG Light Chain of donanemab (SEQ ID NO: 39)
DIVMTQTPLSLSVTPGQPASISCKSSQSLLYSRGKTYLNWLLQKPGQSPQLLIYAV
SKLDSGVPDRFSGSGSGTDFTLKISRVEAEDVGVYYCVQGTHYPFTFGQGTKLEI
KRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC Heavy Chain of an anti-N3pG antibody (SEQ ID NO: 40)
EVQLLESGGGLVQPGGSLRLSCAASGFTFSSYPMSWVRQAPGKGLEWVSAISGS
GGSTYYADSVKGRFTISRDNSKNTLYLQMNSLRAEDTA VYYCAREGGSGSYYN
GFDYWGQGTLVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVD
KKVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCSVMHE
ALHNHYTQKSLSLSPG Light Chain of an anti-N3pG antibody (SEQ ID NO: 41)
DIQMTQSPSTLSASVGDRVTITCRASQSLGNWLAWYQQKPGKAPKLLIYQASTLE
SGVPSRFSGSGSGTEFTLTISSLQPDDFATYYCQHYKGSFWTFGQGTKVEIKRTVA
APSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

We claim:

1. An antibody that binds human IL-34 wherein the antibody comprises a heavy chain variable region (VH) and a light chain variable region (VL), wherein the VH comprises heavy chain complementarity determining regions (HCDR) HCDR1, HCDR2, and HCDR3, and the VL comprises light chain complementarity determining regions (LCDR) LCDR1, LCDR2, and LCDR3, wherein the HCDR1 comprises SEQ ID NO: 5,
the HCDR2 comprises SEQ ID NO: 6,
the HCDR3 comprises SEQ ID NO: 7,
the LCDR1 comprises SEQ ID NO: 8,
the LCDR2 comprises SEQ ID NO: 9, and
the LCDR3 comprises SEQ ID NO: 10.

2. The antibody of claim 1, wherein the VH comprises SEQ ID NO: 3 and the VL comprises SEQ ID NO: 4.

3. The antibody of claim 1 wherein the antibody comprises a heavy chain (HC) comprising SEQ ID NO: 1 and a light chain (LC) comprising SEQ ID NO: 2.

4. An antibody encoded by nucleic acids comprising the nucleotide sequences of SEQ ID NO: 11 and 12, respectively; and produced by a process comprising culturing a mammalian cell comprising the nucleic acids under conditions such that the antibody is expressed, and recovering the expressed antibody from the culture medium.

5. A pharmaceutical composition comprising the antibody of any one of claims 1-3, and a pharmaceutically acceptable excipient, diluent or carrier.

* * * * *